(12) United States Patent
Griffin et al.

(10) Patent No.: US 8,231,551 B2
(45) Date of Patent: *Jul. 31, 2012

(54) ELONGATE MEDICAL DEVICE WITH CONTINUOUS REINFORCEMENT MEMBER

(75) Inventors: Stephen Griffin, San Jose, CA (US); Elaine Lim, Fremont, CA (US); Huey Quoc Chan, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/966,816

(22) Filed: Dec. 13, 2010

(65) Prior Publication Data

US 2011/0082443 A1     Apr. 7, 2011

Related U.S. Application Data

(63) Continuation of application No. 11/260,834, filed on Oct. 27, 2005, now Pat. No. 7,850,623.

(51) Int. Cl.
*A61M 25/00* (2006.01)

(52) U.S. Cl. ............................................. 600/585

(58) Field of Classification Search ............ 600/433, 600/434, 585; 604/164.13
See application file for complete search history.

(56) References Cited

U.S. PATENT DOCUMENTS

| | | |
|---|---|---|
| 1,553,227 A | 9/1925 | Feyk et al. |
| 1,866,888 A | 7/1932 | Hawley |
| 2,275,827 A | 3/1942 | Plensler |
| 2,413,805 A | 1/1947 | Vickers |
| 2,441,166 A | 5/1948 | Raspert |
| 2,561,890 A | 7/1951 | Stoddard |
| 2,722,614 A | 11/1955 | Fryklund |
| 2,857,536 A | 10/1958 | Light |
| 2,864,017 A | 12/1958 | Waltscheff |
| 2,871,793 A | 2/1959 | Michie et al. |
| 3,249,776 A | 5/1966 | Anderson et al. |
| 3,322,984 A | 5/1967 | Anderson |
| 3,334,253 A | 8/1967 | Hill |
| 3,363,470 A | 1/1968 | Yavne |

(Continued)

FOREIGN PATENT DOCUMENTS

AU     723040     12/1997

(Continued)

OTHER PUBLICATIONS

Rothbart, H.A., "Helical Compression Springs," Mechanical Design and Systems Handbook (1964) p. 33-13 (one sheet).

*Primary Examiner* — Max Hindenburg
*Assistant Examiner* — Jonathan M Foreman
(74) *Attorney, Agent, or Firm* — Seager, Tufte & Wickhem, LLC

(57) ABSTRACT

An elongate medical device including an inner elongate member, a reinforcing member, and an outer tubular member is described. The reinforcing member may be a helically wound continuous wire including a first portion having a first cross-sectional profile, a second portion having a second cross-sectional profile, and a transition region located between the first portion and the second portion. The first cross-sectional profile may be different from the second cross-sectional profile. In some embodiments, the first cross-sectional profile may be circular or non-circular and the second cross-sectional profile may be circular or non-circular.

12 Claims, 7 Drawing Sheets

U.S. PATENT DOCUMENTS

| | | |
|---|---|---|
| 3,452,227 A | 6/1969 | Welch |
| 3,452,742 A | 7/1969 | Muller |
| 3,463,953 A | 8/1969 | Maxwell |
| 3,512,019 A | 5/1970 | Durand |
| 3,544,868 A | 12/1970 | Bates |
| 3,625,200 A | 12/1971 | Muller |
| 3,686,990 A | 8/1972 | Margolien |
| 3,841,308 A | 10/1974 | Tate |
| 3,890,977 A | 6/1975 | Wilson |
| 3,906,938 A | 9/1975 | Fleischhacker |
| 4,000,672 A | 1/1977 | Sitterer et al. |
| 4,003,369 A | 1/1977 | Heilman et al. |
| 4,020,829 A | 5/1977 | Willson et al. |
| 4,142,119 A | 2/1979 | Madey |
| 4,215,703 A | 8/1980 | Wilson |
| 4,330,725 A | 5/1982 | Hintz |
| 4,425,919 A | 1/1984 | Alston, Jr. et al. |
| 4,476,754 A | 10/1984 | Ducret |
| 4,482,828 A | 11/1984 | Vergues et al. |
| 4,516,972 A | 5/1985 | Samson |
| 4,545,390 A | 10/1985 | Leary |
| 4,563,181 A | 1/1986 | Wijayarathna et al. |
| 4,574,670 A | 3/1986 | Johnson |
| 4,580,551 A | 4/1986 | Siegmund et al. |
| 4,583,404 A | 4/1986 | Bernard et al. |
| 4,635,270 A | 1/1987 | Gürs |
| 4,665,906 A | 5/1987 | Jervis |
| 4,676,249 A | 6/1987 | Arenas et al. |
| 4,721,117 A | 1/1988 | Mar et al. |
| 4,737,153 A | 4/1988 | Shimamura et al. |
| 4,763,647 A | 8/1988 | Gambale |
| 4,774,949 A | 10/1988 | Fogarty |
| 4,781,092 A | 11/1988 | Gaiser |
| 4,781,186 A | 11/1988 | Simpson et al. |
| 4,786,220 A | 11/1988 | Fildes et al. |
| 4,790,331 A | 12/1988 | Okada et al. |
| 4,800,890 A | 1/1989 | Cramer |
| 4,811,743 A | 3/1989 | Stevens |
| 4,827,941 A | 5/1989 | Taylor et al. |
| 4,831,858 A | 5/1989 | Yoshizawa |
| 4,832,047 A | 5/1989 | Sepetka et al. |
| 4,846,186 A | 7/1989 | Box et al. |
| 4,846,193 A | 7/1989 | Tremulis et al. |
| 4,867,173 A | 9/1989 | Leoni |
| 4,875,489 A | 10/1989 | Messner et al. |
| 4,884,579 A | 12/1989 | Engelson |
| 4,911,148 A | 3/1990 | Sosnowski et al. |
| 4,917,102 A | 4/1990 | Miller et al. |
| 4,922,164 A | 5/1990 | Jacobsen et al. |
| 4,922,777 A | 5/1990 | Kawabata |
| 4,932,959 A | 6/1990 | Horzewski et al. |
| 4,934,380 A | 6/1990 | de Toledo |
| 4,953,553 A | 9/1990 | Tremulis |
| 4,954,022 A | 9/1990 | Underwood et al. |
| 4,955,384 A | 9/1990 | Taylor et al. |
| 4,955,862 A | 9/1990 | Sepetka |
| 4,960,410 A | 10/1990 | Pinchuk |
| 4,964,409 A | 10/1990 | Tremulis |
| 4,966,163 A | 10/1990 | Kraus et al. |
| 4,968,306 A | 11/1990 | Huss et al. |
| 4,973,321 A | 11/1990 | Michelson |
| 4,981,478 A | 1/1991 | Evard et al. |
| 4,985,022 A | 1/1991 | Fearnot et al. |
| 4,989,608 A | 2/1991 | Ratner |
| 4,990,143 A | 2/1991 | Sheridan |
| 4,994,069 A | 2/1991 | Ritchart et al. |
| 4,998,923 A | 3/1991 | Samson et al. |
| 5,007,434 A | 4/1991 | Doyle et al. |
| 5,009,137 A | 4/1991 | Dannatt |
| 5,040,543 A | 8/1991 | Badera et al. |
| 5,050,606 A | 9/1991 | Tremulis |
| 5,052,404 A | 10/1991 | Hodgson |
| 5,059,177 A | 10/1991 | Alcebo et al. |
| 5,063,935 A | 11/1991 | Gamble |
| 5,065,769 A | 11/1991 | De Toledo |
| 5,095,915 A | 3/1992 | Engelson |
| 5,106,455 A | 4/1992 | Jacobsen et al. |
| 5,109,830 A | 5/1992 | Cho |
| 5,125,395 A | 6/1992 | Adair |
| 5,135,531 A | 8/1992 | Shiber |
| 5,144,959 A | 9/1992 | Gambale et al. |
| 5,147,317 A | 9/1992 | Shank et al. |
| 5,176,660 A | 1/1993 | Truckai |
| 5,180,376 A | 1/1993 | Fischell |
| 5,181,668 A | 1/1993 | Tsuji et al. |
| 5,205,830 A | 4/1993 | Dassa et al. |
| 5,211,183 A | 5/1993 | Wilson |
| 5,228,441 A | 7/1993 | Lundquist |
| 5,238,004 A | 8/1993 | Sahatjian et al. |
| 5,242,759 A | 9/1993 | Hall |
| 5,243,996 A | 9/1993 | Hall |
| 5,250,069 A | 10/1993 | Nobuyoshi et al. |
| 5,254,106 A | 10/1993 | Feaster |
| 5,254,107 A | 10/1993 | Soltesz |
| 5,256,144 A | 10/1993 | Kraus et al. |
| 5,257,974 A | 11/1993 | Cox |
| 5,259,393 A | 11/1993 | Corso, Jr. et al. |
| 5,267,979 A | 12/1993 | Appling et al. |
| 5,267,982 A | 12/1993 | Sylvanowicz |
| 5,279,562 A | 1/1994 | Sirhan et al. |
| 5,284,128 A | 2/1994 | Hart |
| 5,300,032 A | 4/1994 | Hibbs et al. |
| 5,304,131 A | 4/1994 | Paskar |
| 5,306,252 A | 4/1994 | Yutori et al. |
| 5,308,435 A | 5/1994 | Ruggles et al. |
| 5,315,906 A | 5/1994 | Ferenczi et al. |
| 5,315,996 A | 5/1994 | Lundquist |
| 5,318,529 A | 6/1994 | Kontos |
| 5,322,064 A | 6/1994 | Lundquist |
| 5,329,923 A | 7/1994 | Lundquist |
| 5,333,620 A | 8/1994 | Moutafis et al. |
| 5,334,145 A | 8/1994 | Lundquist et al. |
| 5,336,205 A | 8/1994 | Zenzen et al. |
| 5,341,818 A | 8/1994 | Abrams et al. |
| 5,345,937 A | 9/1994 | Middleman et al. |
| 5,345,945 A | 9/1994 | Hodgson et al. |
| 5,354,623 A | 10/1994 | Hall |
| 5,358,493 A | 10/1994 | Schweich et al. |
| 5,358,796 A | 10/1994 | Nakamura et al. |
| 5,365,942 A | 11/1994 | Shank |
| 5,365,943 A | 11/1994 | Jansen |
| 5,368,564 A | 11/1994 | Savage |
| 5,368,661 A | 11/1994 | Nakamura et al. |
| 5,376,084 A | 12/1994 | Bacich et al. |
| 5,381,782 A | 1/1995 | DeLaRama et al. |
| 5,406,960 A | 4/1995 | Corso, Jr. |
| 5,411,476 A | 5/1995 | Abrams |
| 5,425,723 A | 6/1995 | Wang |
| 5,437,288 A | 8/1995 | Schwartz et al. |
| 5,438,993 A | 8/1995 | Lynch et al. |
| 5,439,000 A | 8/1995 | Gunderson et al. |
| 5,441,483 A | 8/1995 | Avitall |
| 5,441,489 A | 8/1995 | Utsumi et al. |
| 5,447,812 A | 9/1995 | Fukuda et al. |
| 5,454,787 A | 10/1995 | Lundquist |
| 5,454,795 A | 10/1995 | Samson |
| 5,458,605 A | 10/1995 | Klemm |
| 5,460,187 A | 10/1995 | Daigle et al. |
| 5,460,608 A | 10/1995 | Lodin et al. |
| 5,470,330 A | 11/1995 | Goldenberg et al. |
| 5,476,701 A | 12/1995 | Berger |
| 5,477,856 A | 12/1995 | Lundquist |
| 5,496,294 A | 3/1996 | Hergenrother et al. |
| 5,497,785 A | 3/1996 | Viera |
| 5,507,301 A | 4/1996 | Wasicek et al. |
| 5,507,729 A | 4/1996 | Lindenberg et al. |
| 5,507,751 A | 4/1996 | Goode et al. |
| 5,507,766 A | 4/1996 | Kugo et al. |
| 5,514,128 A | 5/1996 | Hillsman et al. |
| 5,520,194 A | 5/1996 | Miyata et al. |
| 5,520,645 A | 5/1996 | Imran et al. |
| 5,531,719 A | 7/1996 | Takahashi |
| 5,533,985 A | 7/1996 | Wang |
| 5,546,958 A | 8/1996 | Thorud et al. |
| 5,551,444 A | 9/1996 | Finlayson |
| 5,554,139 A | 9/1996 | Okajima |
| 5,562,619 A | 10/1996 | Mirarchi et al. |

| | | | | | | |
|---|---|---|---|---|---|---|
| 5,569,197 | A | 10/1996 | Helmus et al. | 6,022,343 | A | 2/2000 | Johnson et al. |
| 5,569,200 | A | 10/1996 | Umeno et al. | 6,022,369 | A | 2/2000 | Jacobsen et al. |
| 5,569,218 | A | 10/1996 | Berg | 6,024,730 | A | 2/2000 | Pagan |
| 5,571,073 | A | 11/1996 | Castillo | 6,027,461 | A | 2/2000 | Walker et al. |
| 5,573,520 | A | 11/1996 | Schwartz et al. | 6,036,682 | A * | 3/2000 | Lange et al. ............... 604/529 |
| 5,584,821 | A | 12/1996 | Hobbs et al. | 6,042,553 | A | 3/2000 | Solar et al. |
| 5,599,326 | A | 2/1997 | Carter | 6,045,547 | A | 4/2000 | Ren et al. |
| 5,599,492 | A | 2/1997 | Engelson | 6,048,339 | A | 4/2000 | Zirps et al. |
| 5,601,539 | A | 2/1997 | Corso, Jr. | 6,053,903 | A | 4/2000 | Samson |
| 5,603,705 | A | 2/1997 | Berg | 6,056,702 | A | 5/2000 | Lorenzo |
| 5,605,162 | A | 2/1997 | Mirzaee et al. | 6,063,101 | A | 5/2000 | Jacobsen et al. |
| 5,622,184 | A | 4/1997 | Ashby et al. | 6,063,200 | A | 5/2000 | Jacobsen et al. |
| 5,630,806 | A | 5/1997 | Inagaki et al. | 6,066,361 | A | 5/2000 | Jacobsen et al. |
| 5,637,089 | A | 6/1997 | Abrams et al. | 6,106,485 | A | 8/2000 | McMahon |
| 5,656,011 | A | 8/1997 | Uihlein et al. | 6,106,488 | A | 8/2000 | Fleming et al. |
| 5,658,264 | A | 8/1997 | Samson et al. | 6,139,510 | A | 10/2000 | Palermo |
| 5,666,968 | A | 9/1997 | Imran et al. | 6,152,912 | A | 11/2000 | Jansen et al. |
| 5,666,969 | A | 9/1997 | Urick et al. | 6,159,187 | A | 12/2000 | Park et al. |
| 5,669,926 | A | 9/1997 | Aust et al. | 6,165,292 | A | 12/2000 | Abrams et al. |
| 5,674,208 | A | 10/1997 | Berg et al. | 6,171,296 | B1 | 1/2001 | Chow |
| 5,676,659 | A | 10/1997 | McGurk | 6,183,410 | B1 | 2/2001 | Jacobsen et al. |
| 5,676,697 | A | 10/1997 | McDonald | 6,193,686 | B1 | 2/2001 | Estrada et al. |
| 5,680,873 | A | 10/1997 | Berg et al. | 6,197,014 | B1 | 3/2001 | Samson et al. |
| 5,682,894 | A | 11/1997 | Orr et al. | 6,203,485 | B1 | 3/2001 | Urick |
| 5,690,120 | A | 11/1997 | Jacobsen et al. | RE37,148 | E | 4/2001 | Shank |
| 5,702,373 | A | 12/1997 | Samson | 6,212,422 | B1 | 4/2001 | Berg et al. |
| 5,720,300 | A | 2/1998 | Fagan et al. | 6,214,042 | B1 | 4/2001 | Jacobsen et al. |
| 5,722,609 | A | 3/1998 | Murakami | 6,228,073 | B1 | 5/2001 | Noone et al. |
| 5,728,063 | A | 3/1998 | Preissman et al. | 6,248,082 | B1 | 6/2001 | Jafari |
| 5,733,248 | A | 3/1998 | Adams et al. | 6,251,092 | B1 | 6/2001 | Qin et al. |
| 5,741,429 | A | 4/1998 | Donadio, III et al. | 6,254,549 | B1 | 7/2001 | Ramzipoor |
| 5,746,701 | A | 5/1998 | Noone | 6,260,458 | B1 | 7/2001 | Jacobsen et al. |
| 5,769,830 | A | 6/1998 | Parker | 6,273,404 | B1 | 8/2001 | Holman et al. |
| 5,772,609 | A | 6/1998 | Nguyen et al. | 6,273,876 | B1 | 8/2001 | Klima et al. |
| 5,782,809 | A | 7/1998 | Umeno et al. | 6,273,879 | B1 | 8/2001 | Keith et al. |
| 5,788,653 | A | 8/1998 | Lorenzo | 6,290,656 | B1 | 9/2001 | Boyle et al. |
| 5,788,654 | A | 8/1998 | Schwager | 6,296,616 | B1 | 10/2001 | McMahon |
| 5,788,707 | A | 8/1998 | Del Toro et al. | 6,296,631 | B2 | 10/2001 | Chow |
| 5,792,124 | A | 8/1998 | Horrigan et al. | 6,302,870 | B1 | 10/2001 | Jacobsen et al. |
| 5,797,856 | A | 8/1998 | Frisbie et al. | 6,325,790 | B1 | 12/2001 | Trotta |
| 5,800,454 | A | 9/1998 | Jacobsen et al. | 6,338,725 | B1 | 1/2002 | Hermann et al. |
| 5,807,075 | A | 9/1998 | Jacobsen et al. | 6,346,091 | B1 | 2/2002 | Jacobsen et al. |
| 5,807,249 | A | 9/1998 | Qin et al. | 6,352,515 | B1 | 3/2002 | Anderson et al. |
| 5,810,885 | A | 9/1998 | Zinger | 6,355,005 | B1 | 3/2002 | Powell et al. |
| 5,813,996 | A | 9/1998 | St. Germain et al. | 6,355,027 | B1 | 3/2002 | Le et al. |
| 5,827,225 | A | 10/1998 | Ma Schwab | 6,368,315 | B1 | 4/2002 | Gillis et al. |
| 5,827,242 | A | 10/1998 | Follmer et al. | 6,368,316 | B1 | 4/2002 | Jansen et al. |
| 5,830,155 | A | 11/1998 | Frechette et al. | 6,375,628 | B1 | 4/2002 | Zadno-Azizi et al. |
| 5,833,631 | A | 11/1998 | Nguyen | 6,375,774 | B1 | 4/2002 | Lunn et al. |
| 5,833,632 | A | 11/1998 | Jacobsen et al. | 6,379,369 | B1 | 4/2002 | Abrams et al. |
| 5,836,926 | A | 11/1998 | Peterson et al. | 6,390,993 | B1 | 5/2002 | Cornish et al. |
| 5,843,050 | A | 12/1998 | Jones et al. | 6,398,758 | B1 | 6/2002 | Jacobsen et al. |
| 5,843,244 | A | 12/1998 | Pelton et al. | 6,428,489 | B1 | 8/2002 | Jacobsen et al. |
| 5,851,203 | A | 12/1998 | van Muiden | 6,428,512 | B1 | 8/2002 | Anderson et al. |
| 5,853,400 | A | 12/1998 | Samson | 6,431,039 | B1 | 8/2002 | Jacobsen et al. |
| 5,860,963 | A | 1/1999 | Azam et al. | 6,440,088 | B1 | 8/2002 | Jacobsen |
| 5,891,114 | A | 4/1999 | Chien et al. | 6,478,778 | B1 | 11/2002 | Jacobsen et al. |
| 5,895,378 | A | 4/1999 | Nita | 6,488,637 | B1 | 12/2002 | Eder et al. |
| 5,897,537 | A | 4/1999 | Berg et al. | 6,491,648 | B1 | 12/2002 | Cornish et al. |
| 5,902,254 | A | 5/1999 | Magram | 6,491,671 | B1 | 12/2002 | Larson, III et al. |
| 5,902,290 | A | 5/1999 | Peacock, III et al. | 6,503,244 | B2 | 1/2003 | Hayman |
| 5,902,499 | A | 5/1999 | Richerzhagen | 6,508,803 | B1 | 1/2003 | Horikawa et al. |
| 5,904,657 | A | 5/1999 | Unsworth et al. | 6,508,806 | B1 | 1/2003 | Hoste |
| 5,906,618 | A | 5/1999 | Larson, III | 6,524,301 | B1 | 2/2003 | Wilson et al. |
| 5,911,715 | A | 6/1999 | Berg et al. | 6,530,934 | B1 | 3/2003 | Jacobsen et al. |
| 5,911,717 | A | 6/1999 | Jacobsen et al. | 6,547,779 | B2 | 4/2003 | Levine et al. |
| 5,916,177 | A | 6/1999 | Schwager | 6,553,880 | B2 | 4/2003 | Jacobsen et al. |
| 5,916,178 | A | 6/1999 | Noone | 6,556,873 | B1 | 4/2003 | Smits |
| 5,916,194 | A | 6/1999 | Jacobsen et al. | 6,579,246 | B2 | 6/2003 | Jacobsen et al. |
| 5,931,830 | A | 8/1999 | Jacobsen et al. | 6,602,207 | B1 | 8/2003 | Mann et al. |
| 5,935,108 | A | 8/1999 | Katoh et al. | 6,602,280 | B2 | 8/2003 | Chobotov |
| 5,947,940 | A | 9/1999 | Beisel | 6,610,046 | B1 | 8/2003 | Usami et al. |
| 5,951,539 | A | 9/1999 | Nita et al. | 6,623,448 | B2 | 9/2003 | Slater |
| 5,971,975 | A | 10/1999 | Mills et al. | 6,636,758 | B2 | 10/2003 | Sanchez et al. |
| 5,980,471 | A | 11/1999 | Jafari | 6,638,266 | B2 | 10/2003 | Wilson et al. |
| 6,001,068 | A | 12/1999 | Uchino et al. | 6,652,508 | B2 | 11/2003 | Griffin et al. |
| 6,004,279 | A | 12/1999 | Crowley et al. | 6,682,493 | B2 | 1/2004 | Mirigian |
| 6,014,919 | A | 1/2000 | Jacobsen et al. | 6,689,120 | B1 | 2/2004 | Gerdts |
| 6,017,319 | A | 1/2000 | Jacobsen et al. | 6,702,762 | B2 | 3/2004 | Jafari et al. |

| | | | | | | |
|---|---|---|---|---|---|---|
| 6,712,826 B2 | 3/2004 | Lui | | EP | 0 778 040 | 6/1997 |
| 6,730,095 B2 | 5/2004 | Olson, Jr. et al. | | EP | 0 790 066 | 8/1997 |
| 6,749,560 B1 | 6/2004 | Konstorum et al. | | EP | 0 812 599 | 12/1997 |
| 6,766,720 B1 | 7/2004 | Jacobsen et al. | | EP | 0 820 782 | 1/1998 |
| 6,777,644 B2 | 8/2004 | Peacock, III et al. | | EP | 0 865 772 | 9/1998 |
| 6,811,544 B2 | 11/2004 | Schaer | | EP | 0 865 773 | 9/1998 |
| 6,837,898 B2 | 1/2005 | Boyle et al. | | EP | 0 917 885 | 5/1999 |
| 6,866,642 B2 | 3/2005 | Kellerman et al. | | EP | 0 937 481 | 8/1999 |
| 6,866,665 B2 | 3/2005 | Orbay | | EP | 0 935 947 | 12/2004 |
| 6,887,235 B2 | 5/2005 | O'Connor et al. | | EP | 0 934 141 | 11/2005 |
| 6,918,882 B2 | 7/2005 | Skujins et al. | | GB | 2214354 | 8/1989 |
| 6,997,937 B2 | 2/2006 | Jacobsen et al. | | GB | 2257269 | 1/1993 |
| 7,001,369 B2 | 2/2006 | Griffin et al. | | JP | 58-8522 | 1/1983 |
| 7,071,197 B2 | 7/2006 | Leonardi et al. | | JP | 60091858 | 5/1985 |
| 7,074,197 B2 | 7/2006 | Reynolds et al. | | JP | 61022752 | 1/1986 |
| 7,153,277 B2 | 12/2006 | Skujins et al. | | JP | 62023361 | 1/1987 |
| 7,169,118 B2 | 1/2007 | Reynolds et al. | | JP | 62089470 | 4/1987 |
| 7,182,735 B2 | 2/2007 | Shireman et al. | | JP | 62299277 | 12/1987 |
| 7,850,623 B2 * | 12/2010 | Griffin et al. ............... 600/585 | | JP | 6393516 | 4/1988 |
| 2002/0013540 A1 | 1/2002 | Jacobsen et al. | | JP | 63-181774 | 7/1988 |
| 2002/0019599 A1 | 2/2002 | Rooney et al. | | JP | 63217966 | 9/1988 |
| 2003/0009208 A1 | 1/2003 | Snyder et al. | | JP | 1089956 | 4/1989 |
| 2003/0060732 A1 | 3/2003 | Jacobsen et al. | | JP | 1135363 | 5/1989 |
| 2003/0069522 A1 | 4/2003 | Jacobsen et al. | | JP | 1158936 | 6/1989 |
| 2003/0216668 A1 | 11/2003 | Howland et al. | | JP | 2107268 | 4/1990 |
| 2004/0010243 A1 | 1/2004 | Klint | | JP | 03-122850 | 12/1991 |
| 2004/0045645 A1 | 3/2004 | Zhou | | JP | 751067 | 12/1991 |
| 2004/0082879 A1 | 4/2004 | Klint | | JP | 4061840 | 2/1992 |
| 2004/0116831 A1 | 6/2004 | Vrba | | JP | 4099963 | 3/1992 |
| 2004/0142643 A1 | 7/2004 | Miller et al. | | JP | 4213069 | 8/1992 |
| 2004/0167436 A1 | 8/2004 | Reynolds et al. | | JP | 4213070 | 8/1992 |
| 2004/0167437 A1 | 8/2004 | Sharrow et al. | | JP | 4236965 | 8/1992 |
| 2004/0167440 A1 | 8/2004 | Sharrow | | JP | 5149969 | 6/1993 |
| 2004/0167441 A1 | 8/2004 | Reynolds et al. | | JP | 5-506806 | 10/1993 |
| 2004/0181174 A2 | 9/2004 | Davis et al. | | JP | 5-309519 | 11/1993 |
| 2004/0181176 A1 | 9/2004 | Jafari et al. | | JP | 5-507857 | 11/1993 |
| 2004/0181207 A1 | 9/2004 | Vitullo et al. | | JP | 631749 | 4/1994 |
| 2004/0193140 A1 | 9/2004 | Griffin et al. | | JP | 6169996 | 6/1994 |
| 2005/0027309 A1 | 2/2005 | Shiber | | JP | 6-63224 | 9/1994 |
| 2005/0177073 A1 | 8/2005 | Shiber | | JP | 6312313 | 11/1994 |
| 2006/0111649 A1 | 5/2006 | Zhou | | JP | 728562 | 5/1995 |
| 2006/0121218 A1 | 6/2006 | Obara et al. | | JP | 7124164 | 5/1995 |
| 2006/0122537 A1 | 6/2006 | Reynolds et al. | | JP | 7124263 | 5/1995 |
| 2006/0189896 A1 | 8/2006 | Davis et al. | | JP | 7136280 | 5/1995 |
| 2006/0264904 A1 | 11/2006 | Kerby et al. | | JP | 7148264 | 6/1995 |
| 2007/0100424 A1 | 5/2007 | Chew et al. | | JP | 7505561 | 6/1995 |
| 2008/0021347 A1 | 1/2008 | Jacobsen et al. | | JP | 7037199 | 7/1995 |
| 2008/0021348 A1 | 1/2008 | Jacobsen et al. | | JP | 7185009 | 7/1995 |
| 2008/0021400 A1 | 1/2008 | Jacobsen et al. | | JP | 7255855 | 10/1995 |
| 2008/0021401 A1 | 1/2008 | Jacobsen et al. | | JP | 7275366 | 10/1995 |
| 2008/0021402 A1 | 1/2008 | Jacobsen et al. | | JP | 8-229888 | 9/1996 |
| 2008/0021403 A1 | 1/2008 | Jacobsen et al. | | JP | 8509141 | 10/1996 |
| 2008/0021404 A1 | 1/2008 | Jacobsen et al. | | JP | 8-317988 | 12/1996 |
| 2008/0021405 A1 | 1/2008 | Jacobsen et al. | | JP | 9000164 | 4/1997 |
| 2008/0021406 A1 | 1/2008 | Jacobsen et al. | | JP | 9-276413 | 10/1997 |
| 2008/0021407 A1 | 1/2008 | Jacobsen et al. | | JP | 9-294813 A | 11/1997 |
| 2008/0021408 A1 | 1/2008 | Jacobsen et al. | | JP | 10-118193 | 5/1998 |
| 2008/0077119 A1 | 3/2008 | Snyder et al. | | JP | 10328191 | 12/1998 |
| 2009/0043283 A1 | 2/2009 | Turnlund | | JP | 11-267224 A | 10/1999 |
| | | | | JP | 3081831 | 10/1999 |
| FOREIGN PATENT DOCUMENTS | | | | JP | 2000-197704 A | 7/2000 |
| AU | 733966 | 4/1998 | | JP | 2000-510722 A | 8/2000 |
| BR | 9712829 | 1/2000 | | JP | 2000-511083 A | 8/2000 |
| CA | 2266685 | 5/2006 | | JP | 2001-500808 A | 1/2001 |
| CA | 2255781 | 3/2007 | | JP | 3325828 | 7/2002 |
| CN | 1230914 | 10/1999 | | JP | 2002-529137 A | 9/2002 |
| DE | 285514 | 12/1990 | | JP | 2002-542901 A | 12/2002 |
| EP | 0 045 931 | 2/1982 | | JP | 2002-543896 A | 12/2002 |
| EP | 0 069 522 | 1/1983 | | JP | 2003-517893 A | 6/2003 |
| EP | 0 087 933 | 9/1983 | | JP | 3649604 | 2/2005 |
| EP | 0 111 044 | 6/1984 | | JP | 2005-534407 | 11/2005 |
| EP | 0 181 174 | 5/1986 | | SU | 712908 | 1/1980 |
| EP | 0 215 173 | 3/1987 | | SU | 758421 | 8/1980 |
| EP | 0 377 453 | 7/1990 | | SU | 1529365 | 12/1989 |
| EP | 0 521 595 | 1/1993 | | WO | WO 90/02520 | 3/1990 |
| EP | 0 565 065 | 10/1993 | | WO | WO 91/13364 | 9/1991 |
| EP | 0 608 853 | 8/1994 | | WO | WO 92/07619 | 5/1992 |
| EP | 0 778 038 | 6/1997 | | WO | WO 93/04722 | 3/1993 |
| EP | 0 778 039 | 6/1997 | | WO | WO 93/11313 | 6/1993 |

| | | | | | | |
|---|---|---|---|---|---|---|
| WO | WO 95/24236 | 9/1995 | | WO | WO 00/67845 | 11/2000 |
| WO | WO 95/32834 | 12/1995 | | WO | WO 00/72907 | 12/2000 |
| WO | WO 96/19255 | 6/1996 | | WO | WO 01/28620 | 4/2001 |
| WO | WO 96/38193 | 12/1996 | | WO | WO 01/36034 | 5/2001 |
| WO | WO 97/10022 | 3/1997 | | WO | WO 01/45773 | 6/2001 |
| WO | WO 97/25914 | 7/1997 | | WO | WO 01/45912 | 6/2001 |
| WO | WO 97/43949 | 11/1997 | | WO | WO 01/93920 | 12/2001 |
| WO | WO 97/44083 | 11/1997 | | WO | WO 02/13682 | 2/2002 |
| WO | WO 97/44086 | 11/1997 | | WO | WO 02/062540 | 8/2002 |
| WO | WO 98/10694 | 3/1998 | | WO | WO 03/004086 | 1/2003 |
| WO | WO 99/04847 | 2/1999 | | WO | WO 03/008148 | 1/2003 |
| WO | WO 99/11313 | 3/1999 | | WO | WO 03/041783 | 5/2003 |
| WO | WO 00/27303 | 5/2000 | | WO | WO 2004/012804 | 2/2004 |
| WO | WO 00/30710 | 6/2000 | | WO | WO 2004/047899 | 6/2004 |
| WO | WO 00/48645 | 8/2000 | | WO | WO 2007/050718 | 5/2007 |
| WO | WO 00/57943 | 10/2000 | | WO | WO 2008/034010 | 3/2008 |
| WO | WO 00/66199 | 11/2000 | | | | |

* cited by examiner

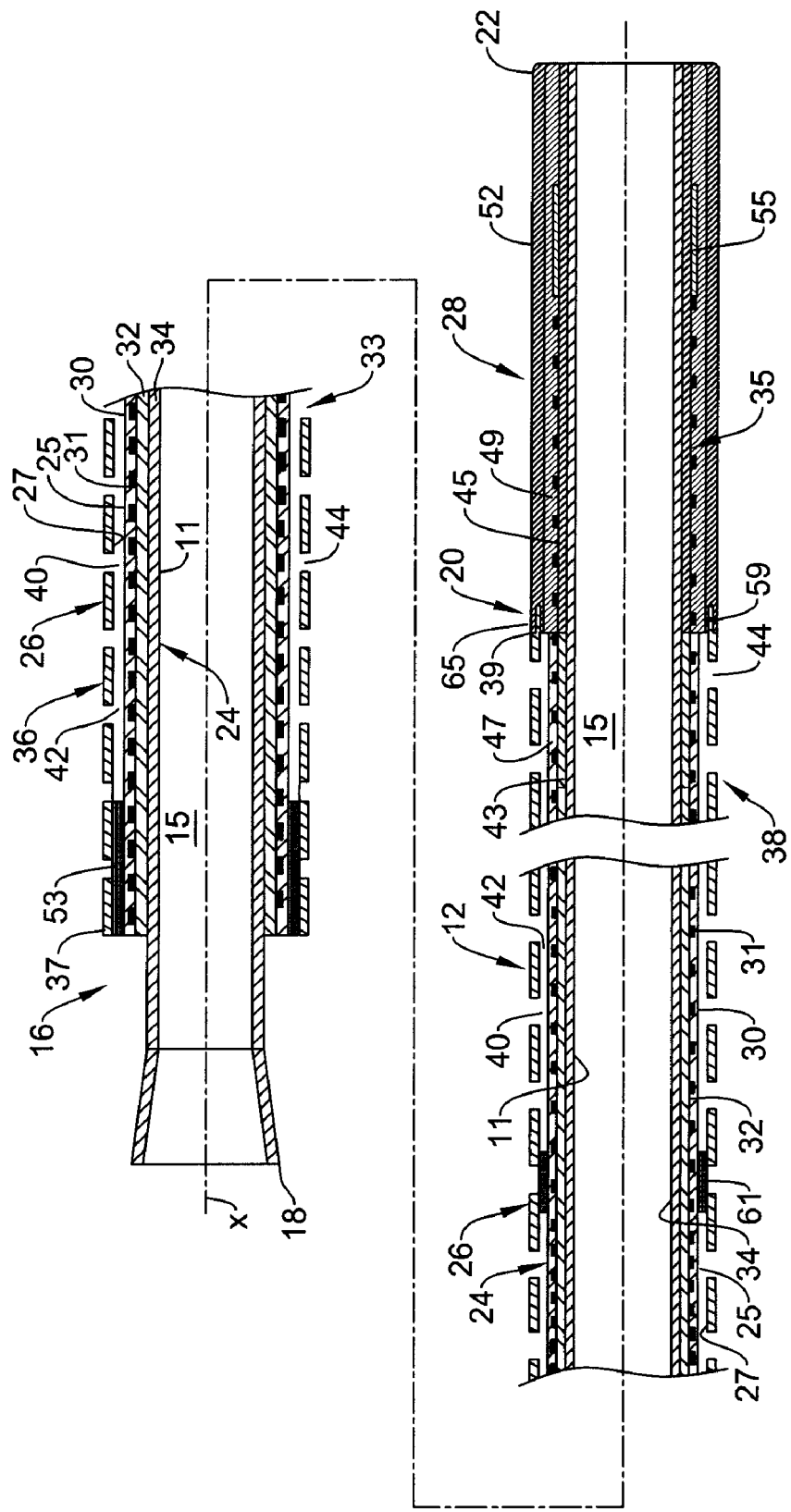

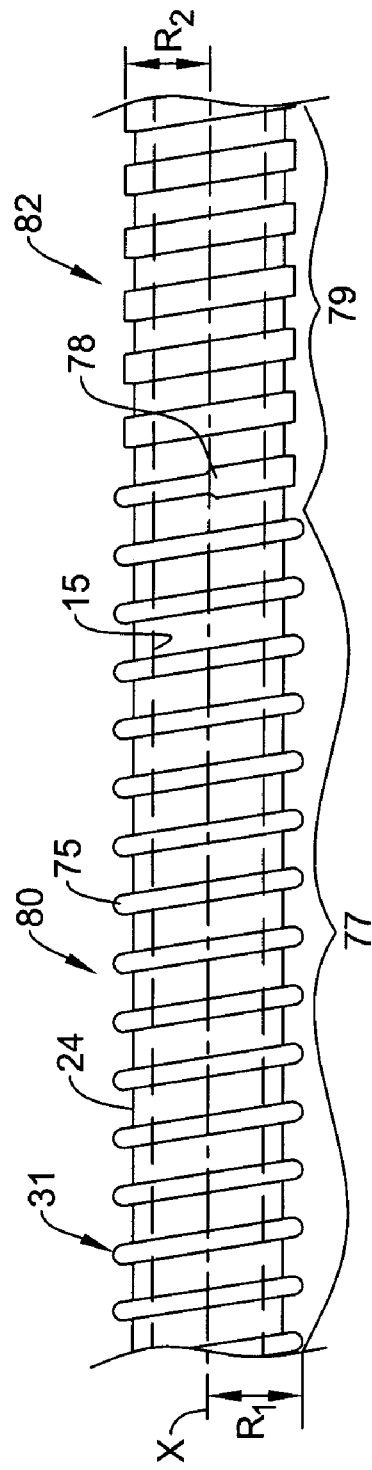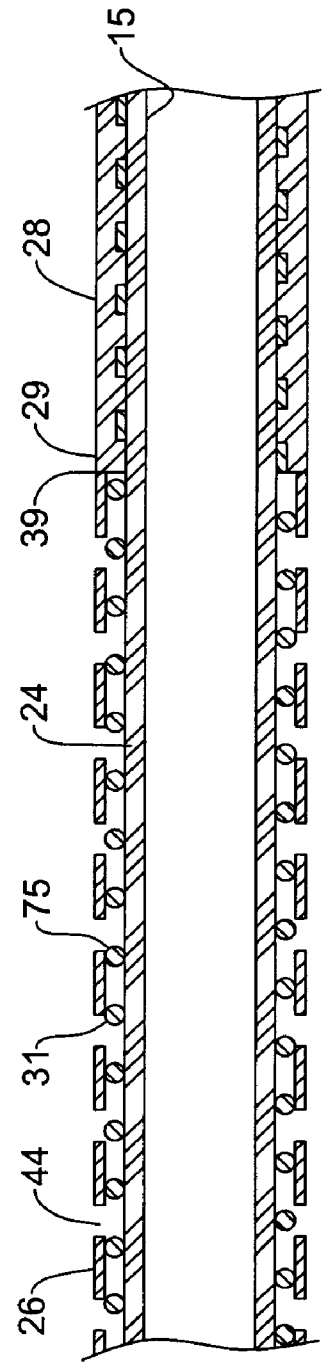
Figure 4A
Figure 4B

ELONGATE MEDICAL DEVICE WITH CONTINUOUS REINFORCEMENT MEMBER

RELATED APPLICATIONS

This application is a continuation of co-pending U.S. application Ser. No. 11/260,834, filed Oct. 27, 2005, the entire disclosure of which is incorporated herein by reference.

TECHNICAL FIELD

The invention relates generally to elongate medical devices. More specifically, the invention relates to an elongate medical device having a continuous reinforcement member.

BACKGROUND

Elongated medical devices are commonly used to facilitate navigation through and/or treatment within the anatomy of a patient. A variety of elongate medical devices for intraluminal use, such as catheters, endoscopes, guidewires and the like, have been developed over the past several decades. Because the anatomy of a patient may be very tortuous, it is often desirable to combine a number of performance features in such devices. For example, it is sometimes desirable that the device have a relatively high level of pushability and torqueability, particularly near its proximal end. It is also sometimes desirable that a device be relatively flexible, particularly near its distal end. A number of different elongated medical device structures and assemblies are known, each having certain advantages and disadvantages. However, there is an ongoing need to provide alternative elongated medical device structures, assemblies, and methods.

SUMMARY

The invention provides design, material, and manufacturing method alternatives for medical devices, such as catheters, guidewires, and the like. Some embodiments may relate to alternative shaft structures, assemblies, and methods for elongated medical devices, such as catheters or guidewires.

Accordingly, some embodiments may include an inner elongate member, a continuous wire disposed about at least a portion of the inner elongate member, and an outer tubular member disposed about at least a portion of the inner elongate member including the continuous wire. In one preferred embodiment, the outer tubular member has a generally constant inside diameter and does not conform to or fill the spaces between turns of the continuous wire. In some embodiments, the continuous wire may include a first section having a first cross-sectional profile, a second section having a second cross-sectional profile different from the first section, and a transition region between the first section and the second section. The first cross-sectional profile may or may not have a cross-sectional area different from the cross-sectional area of the second cross-sectional profile.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments in connection with the accompanying drawings, in which:

FIG. 3 is a partial cross-sectional view of a portion of the shaft of the medical device of FIG. 1, including one example of a distal tip configuration;

FIG. 4A is a plan view of a portion of the medical device of FIG. 1 with any layers overlaying a reinforcing layer removed, thus exposing a continuous reinforcement member helically wound about a portion of an inner elongate member of the shaft;

FIG. 4B is a partial cross-sectional view of the portion of the medical device shown in FIG. 4A and including additional tubular members overlaying the continuous reinforcement member;

Figure 1:
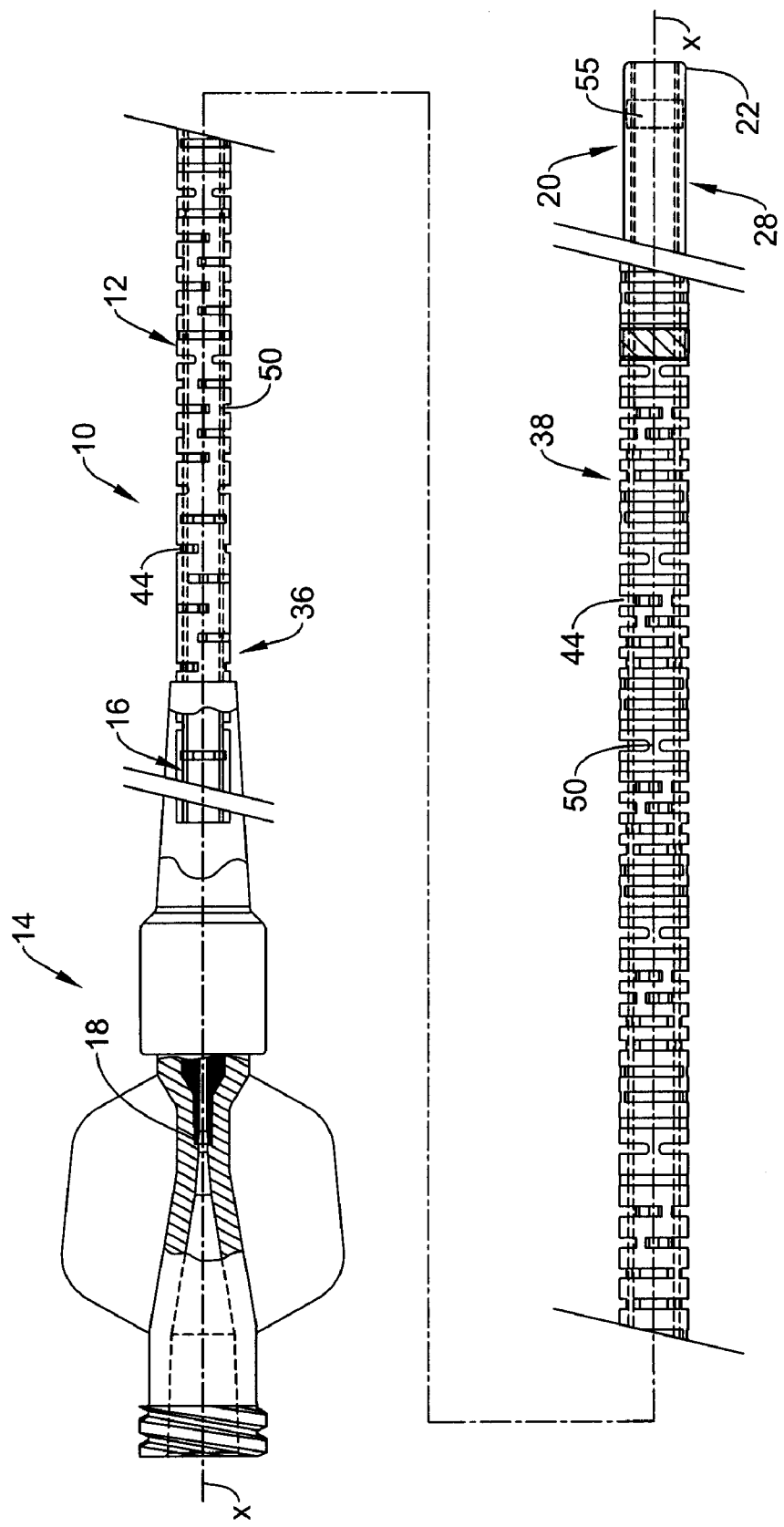
FIG. 1 is a partial side plan view of a medical device in accordance with one example embodiment of the invention shown as a catheter, for example a delivery, guide or diagnostic catheter.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
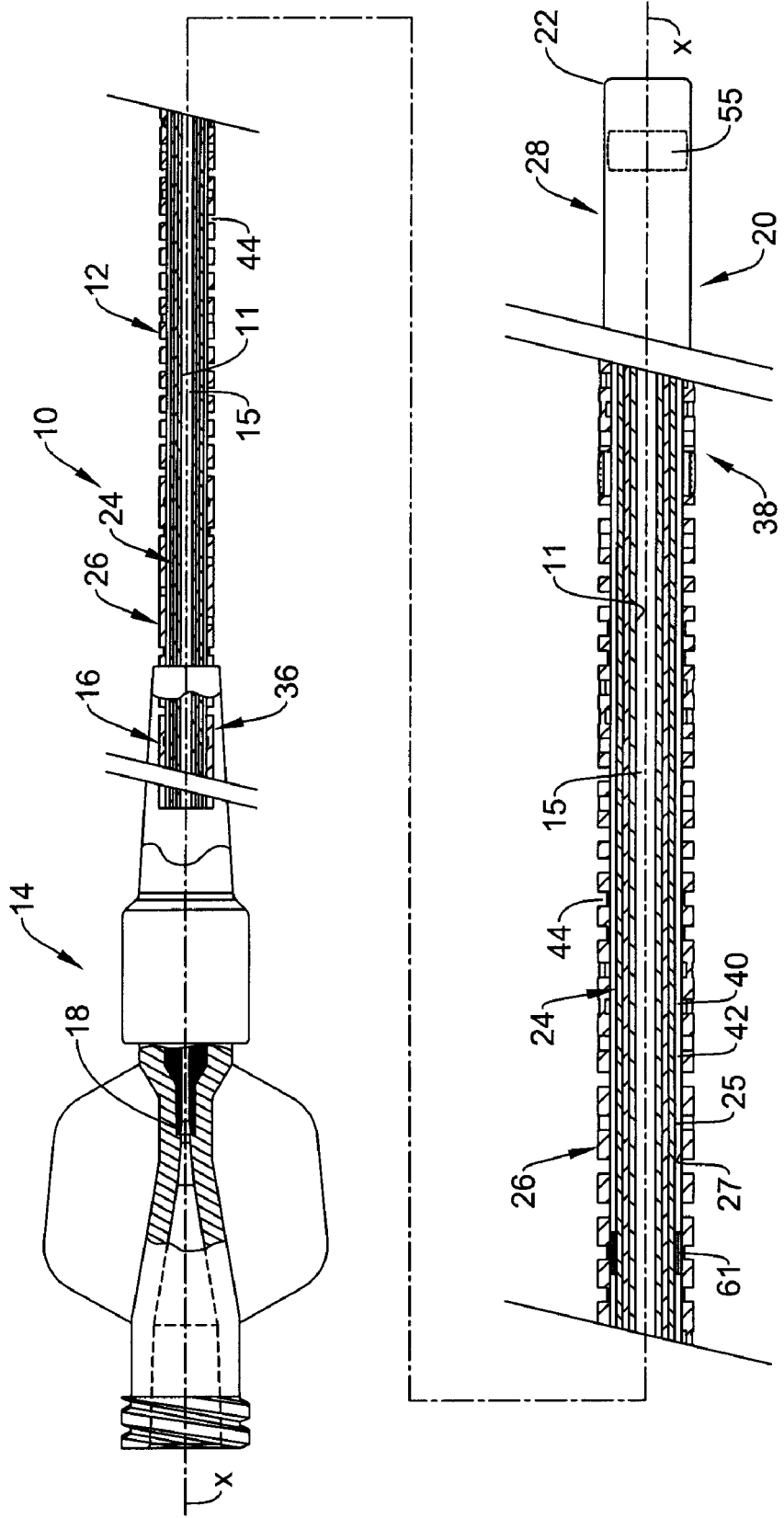
FIG. 2 is a partial cross-sectional view of a portion of the medical device of FIG. 1.

Refer now to FIGS. 1 and 2, which illustrate a medical device 10 in accordance with one example embodiment. In general, the medical device may be a catheter 10, and can include a generally elongate shaft 12 extending along a central or longitudinal axis x. The axis x extends along the length of the catheter 10 and necessarily follows the shape and/or curvature of the shaft 12. The shaft 12 can include a proximal portion 16 having a proximal end 18, and a distal portion 20 having a distal end 22. A distal tip 28 may be disposed at the distal portion 20, and a manifold assembly 14 may be connected at the proximal portion 16 near proximal end 18.

As an initial matter, it should be appreciated that while the medical device 10 is depicted as an intravascular catheter 10, and in particular, an intravascular delivery, guide and/or diagnostic catheter 10, this is for the purposes of illustration only. Other medical devices embodying aspects of the invention may relate to virtually any medical device including an elongate shaft. For example, other embodiments may relate to medical devices such as a balloon catheter, an atherectomy catheter, a drug delivery catheter, a stent delivery catheter, an endoscope, an introducer sheath, a fluid delivery device, other infusion or aspiration devices, device delivery (i.e., implantation) devices, guidewires and the like. Thus, while the Figures and descriptions below are directed toward a delivery, guide, and/or diagnostic catheter, in other applications the structure and/or sizes in terms of diameter and length may vary widely, depending upon the desired properties of a particular device.

Additionally, it should be appreciated that the shaft 12, manifold assembly 14, and distal tip 28 can generally include any of a broad variety of structures and/or configurations. It should be understood that the particular configurations and structures shown and described herein are by way of example only, and that a broad variety of alternative structures and/or configurations may be used without departing from the spirit and scope of the invention as claimed.

The shaft 12 can be manufactured, include structure, and be made of materials so as to provide the desired characteristics of the catheter 10, depending upon the intended use. For example, the shaft 12 can be provided and/or manufactured so as to maintain a desired level of flexibility, torqueability and/or other characteristics appropriate for maneuvering the catheter 10 as desired, for example, through the vasculature of a patient. As such, it should be understood that there is a broad range of possible shaft constructions that may be used, including those particularly discussed herein and others. Some other examples of suitable catheter shaft constructions and materials can be found in U.S. Pat. Nos. 5,569,218; 5,603,705; 5,674,208; 5,680,873; 5,733,248; 5,853,400; 5,860,963; 5,911,715; and 6,866,665, all of which are incorporated herein by reference. Some additional examples of shaft constructions include those disclosed in U.S. patent application Ser. No. 10/238,227 (Publication No. US-2004/0045645), which is also incorporated herein by reference.

The shaft 12 may have a length and an outside diameter appropriate for its desired use, for example, to enable intravascular insertion and navigation. For example, in some embodiments, the shaft 12 may have a length in the range of about 1 cm to about 300 cm or more, or in some embodiments in the range of about 20 cm to about 250 cm, and an outside diameter in the range of about 1 F to about 20 F, or in some embodiments, in the range of about 1 F to about 10 F. Additionally, although depicted as including a generally round outer diameter and a round cross-sectional shape, it can be appreciated that the shaft 12 can include other outer diameter and/or cross-sectional shapes or combinations of shapes without departing from the spirit of the invention. For example, the outer diameter and/or cross-sectional shape of the generally tubular shaft 12 may be oval, rectangular, square, triangular, polygonal, and the like, or combinations thereof, or any other suitable shape, depending upon the desired characteristics.

In some embodiments, the catheter 10 can be a microcatheter including a shaft 12 that is adapted and/or configured for use within small anatomies of the patient. For example, some embodiments are particularly useful in treating target sites located in tortuous and/or narrow vessels. Some examples of such vessels may include those in the neurovascular system, or in certain sites within the coronary vascular system, or in sites within the peripheral vascular system such as superficial femoral, popliteal, or renal arteries. The target site in some embodiments is a neurovascular site, such as a site in the brain, which is accessible only via a tortuous vascular path, for example, a vascular path containing a plurality of bends or turns which may be greater than about 90° turns, and/or involving vessels which are in the range of about 8 mm or less, and in some cases as small as about 2 to about 3 mm or less, in diameter. As such, in some embodiments, the shaft 12 can include an outside diameter in the range of approximately 1 F-4 F.

However, in other embodiments, the catheter 10 may be used in other target sites within the anatomy of a patient, in which case the shaft 12 would be so adapted. For example, the catheter 10 may be suited for other uses in the digestive system, soft tissues, or any other use including insertion into an organism for medical uses, and the shaft 12 could be appropriately adapted for such uses. For example, in some embodiments, the catheter 10 may be used as an introducer sheath, in which case the shaft 12 may be significantly shorter. The catheter 10 may also include additional structure and materials adapted for a particular use and/or procedure. For example, in some other embodiments, the shaft 12 may include additional devices or structures such as inflation or anchoring members, device deployment members, sensors, optical elements, ablation devices, or the like, or any of a broad variety of other structures, depending upon the desired function and characteristics of the catheter 10.

Referring now to FIG. 2, in at least some embodiments, the shaft 12 can have a generally tubular construction that includes at least one lumen 15 extending the length of the shaft 12 along the longitudinal axis x. This can also be seen with reference to FIG. 3, which is a partial cross-sectional view of the shaft. The lumen 15 can be defined by an inner surface 11 of the shaft 12, and can have an inner diameter capable of transmitting fluids, or in some cases, receiving another medical device, such as a guidewire, a stent, a coil (such as an embolic coil, or the like), treatment particles (such as embolic particles, or the like), an ablation device, or another catheter, for example, a diagnostic catheter, a balloon catheter, a stent delivery catheter, or the like, or others. In some embodiments, the lumen 15 can be adapted and/or configured to accommodate another medical device having an outer diameter in the range of about 1 F to about 10 F.

In one embodiment, the shaft 12 includes a generally tubular construction including an inner tubular assembly and/or member 24, and an outer tubular assembly and/or member 26 disposed about at least a portion of the inner tubular member 24; however it should be understood that this is by way of example only. The inner tubular member 24 at least partially defines the inner surface 11 of the shaft 12, and thus defines the lumen 15.

The inner tubular member 24 can extend from a point within the distal portion 20 to a point within the proximal portion 16 of the shaft 12. The length of the inner tubular member 24 can vary depending upon, for example, the length of the shaft 12, the desired characteristics and functions of the inner tubular member 24, and other such parameters. In some embodiments, the inner tubular member 24 can extend substantially the entire length of the shaft 12, for example, from a point adjacent the proximal end 18 to a point adjacent the distal end 22. For example, the length of the inner tubular member 24 can be in the range of about 1-300 centimeters or more, or in some embodiments in the range of about 20 cm-250 cm.

Referring to FIG. 3, the inner tubular member 24 can include a proximal portion 33 and a distal portion 35. The proximal and distal portions 33/35 can be any proximal or distal sections of the inner tubular member 24. However, in some cases the portions 33/35 can be defined with regard to the relative position of the inner and outer tubular members 24/26. For example, the distal portion 35 can be any portion of the inner tubular member 24 that extends distally beyond the distal end 39 of the outer tubular member 26, while the proximal portion 33 can be any portion of the inner tubular member 24 that is disposed within, or is proximal of a distal end 39 of the outer tubular member 26. In some embodiments inner tubular member 24 may extend proximal of the proximal end of the outer tubular member 26 to provide a length of tubing to facilitate attachment of the shaft 12 with a hub assembly 14, or the like. In some embodiments, the distal portion 35 may be the portion of the inner tubular member 24 distal of the transition region (FIGS. 4A, 5A) of the continuous wire of a reinforcing layer 31, and the proximal portion 33 may be the portion of the inner tubular member 24 proximal the transition region. In some embodiments, the distal portion 35 can have a length in the range of about 0.5 cm or greater, or in the range of about 1 cm or greater, or in the range of about 2 cm or greater, and in some embodiments in the range of about 3 to about 20 cm or in the range of about 1.0 to about 1.5 cm. In some embodiments, the distal portion 35 can be disposed within, and/or be a part of, or otherwise include a distal tip 28 construction, some examples of which will be discussed in more detail below.

The inner tubular member 24 may have an inner diameter, for example, defining the lumen 15, that is in the range of about 0.01 to about 0.05 inch in size, or in the range of about 0.015 to about 0.03 inch in size, or in the range of about 0.016 to about 0.026 inch in size. As indicated above, however, the lumen 15 (defined by the inner diameter of the inner tubular member 24) can be adapted and/or configured (e.g., sized) to accept other material, fluids, or medical devices, therein, and as such, the size of the lumen 15 can vary, depending upon the desired characteristics and intended use.

Additionally, the inner tubular member 24 can have an outer diameter that is in the range of about 0.011 inch to about 0.055 inch in size, or in the range of about 0.015 inch to about 0.03 inch in size, or in the range of about 0.019 inch to about 0.029 inch in size. It should be understood, however, that these dimensions are provided by way of example embodiments only and that in other embodiments, the size of the inner and outer diameter of the inner tubular member 24 can vary greatly from the dimensions given, depending upon the desired characteristics and function of the device.

The inner tubular member 24, or other portions of the shaft 12, may define one or more additional lumens depending upon the desired characteristics and function of the catheter 10, and such additional lumens can be shaped, sized, adapted and/or configured the same as or different from lumen 15, depending upon the desired characteristic and functions.

The inner tubular member 24 may include and/or be made of any of a broad variety of materials and/or structures. The inner tubular member 24 may have a single-layer tubular construction or a multi-layer tubular construction, or a combination thereof. For example, the inner tubular member 24 may be a single tubular member formed by a single layer of material, or in other embodiments, may be formed by a plurality of tubular members and/or a plurality of layers of material that may be the same and/or different, but in combination form the inner tubular member 24. In yet other embodiments, some portions of the inner tubular member 24 can include a single layer construction, while other portions may include a multi-layer construction. Some examples of suitable materials can include, but are not limited to, polymers, metals, metal alloys, or composites or combinations thereof.

Some examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro(propyl vinyl ether) (PFA), polyether-ester, some adhesive resin, such as modified polyolefin resin, polymer/metal composites, etc., or mixtures, blends or combinations thereof, and may also include or be made up of a lubricous polymer. Some other potentially suitable polymer materials may include those listed below with reference to the outer tubular member 26. One example of a suitable polyether block ester is available under the trade name ARNITEL, and one suitable example of a polyether block amide (PEBA) is available under the trade name PEBAX®, from ATOM-CHEM POLYMERS, Birdsboro, Pa. In some embodiments, adhesive resins may be used, for example, as tie layers and/or as the material of the structures. One example of a suitable adhesive resin is a modified polyolefin resin available under the trade name ADMER®, from Mitsui Chemicals America, Inc. Additionally, polymer material can in some instances be blended with a liquid crystal polymer (LCP). For example, in some embodiments, the mixture can contain up to about 5% LCP. This has been found in some embodiments to enhance torqueability.

Some examples of suitable metals and metal alloys can include stainless steel, such as 304V, 304L, and 316L stainless steel; nickel-titanium alloy such as a superelastic (i.e., pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it is desirable to use metals, or metal alloys that are suitable for metal joining techniques such as welding, soldering, brazing, crimping, friction fitting, adhesive bonding, etc.

Referring to FIG. 3, at least a portion of the inner tubular member 24 can have a multi-layer tubular construction. The example shown includes an inner layer 34, an intermediate layer 32 disposed about the inner layer 34, a reinforcing layer 31 disposed about the intermediate layer 32, and an outer layer 30 disposed about the reinforcing layer 31 and the intermediate layer 32. It should be understood that more or fewer layers can be used, with or without one or more reinforcing layers, depending upon the desired characteristics of the inner tubular member 24. Additionally, in other embodiments, the layers could be arranged differently to achieve desired properties. For example, the reinforcing layer 31 could be disposed at a different radial location, could be disposed entirely within another layer, could be disposed on the outer surface of the inner tubular member 24, or, as indicated above, could simply be absent. For example, inner tubular member 24 may be a single or multi-layer member having a discrete reinforcing layer 31 such as a wire coil disposed about inner tubular member 24 along at least a portion of the length of the inner tubular member 24. Furthermore, while the layers 30, 32 and 34 are described, these layers may be provided separately but form a single and/or unitary layer and/or structure. Some or all of the plurality of layers, for example layers 30, 31, 32, 34, may be made of any suitable material, for example, those discussed above for use in the inner tubular member 24.

In some embodiments, the inner layer 34 may include a lubricious polymer such as HDPE or PTFE, for example, or a copolymer of tetrafluoroethylene with perfluoroalkyl vinyl ether (PFA) (more specifically, perfluoropropyl vinyl ether or perfluoromethyl vinyl ether), or the like. In some particular embodiments, a PTFE tube is used as the inner layer 34, which can extend the length of the inner tubular member 24.

Furthermore, in some embodiments, the intermediate and outer layers 32/30 may each individually include a flexible polymer, for example a polymer material having a durometer in the range of about 5 D to about 90 D. For example, the intermediate and/or outer layers 32/30 can include or be made up of one or more tubular segments of a PEBA, a polyetherester elastomer, or other like material. The durometer of the material used to form the intermediate and/or outer layers 32/30 may be the same, or may vary from one another, depending upon the characteristics desired. For example, the intermediate layer 32 may be made of a material having a higher durometer than the material of the outer 30 layer along at least a portion of the inner tubular member 24. In other embodiments, the reverse may be true, and in yet other embodiments, the two layers 30/32 may include the material having the same or similar flexibility characteristics.

In some embodiments, one or both of the layers 30/32 can be made up of a plurality of tubular segments including materials having different flexibility characteristics to impart varying degrees of flexibility to different longitudinal sections of the intermediate and/or outer layers 32/30. For example, in some embodiments, one or both of the layers 30/32 can include one or more proximal segments (e.g., 43/47) and one or more distal segments (e.g., 45/45). In some cases, the one or more proximal segments (e.g., 43/47) in either one or both layers 30/32 may include material having a higher durometer than the material included in the distal segment (e.g., 45/45) of each or both respective layer 30/32. Such a construction may be used, for example, to render a more distal portion of the inner tubular member 24 more flexible. Such an arrangement can also be helpful, for example, in providing a flexible distal tip construction, or a portion thereof.

For example, referring to the embodiment shown in FIG. 3, the intermediate layer 32 may include a proximal portion 43 including and/or made of a flexible polymer, such as a PEBA, a polyether-ester elastomer, or other like material, having a durometer in the range of about 40 D to about 70 D. The intermediate layer 32 may also include a distal portion 45 including and/or made of a flexible polymer having a durometer in the range of about 15 D to about 35 D. Additionally, the outer layer 30 may include a proximal portion 47 including and/or made of such a flexible polymer having a durometer in the range of about 25 D to about 55 D. The outer layer 30 may also include a distal portion 49 including and/or made of such a flexible polymer having a durometer in the range of about 15 D to about 35 D.

The inner tubular member 24 can be constructed using any one or a combination of appropriate methods and/or techniques, for example, extrusion, co-extrusion, interrupted layer co-extrusion (ILC), heat bonding techniques, heat shrink techniques, fusing, winding, disposing, adhesive bonding, mechanical bonding, soldering, welding, molding, casting, or the like, or others. In some embodiments, one or more of the layers and/or structures 30/31/32/34 can be formed separately, and thereafter coupled and/or connected together, while in some embodiments, one or more of the layers and/or structures 30/31/32/34 can be formed together using suitable techniques.

For example, in some embodiments, the layers and/or structures 30/31/32/34 can be formed separately, such as by extrusion, co-extrusion, interrupted layer co-extrusion (ILC), casting, molding, heat shrink techniques, fusing, winding, or the like, and thereafter coupled or connected together using suitable techniques, such as heat shrink techniques, friction fitting, mechanically fitting, chemically bonding, thermally bonding, welding (e.g., resistance, Rf, or laser welding), soldering, brazing, adhesive bonding, crimping, or the use of a connector member or material, or the like, or combinations thereof, to form the inner tubular member 24.

In some other embodiments, one or more of the layers and/or structures of the inner tubular member may be formed together at the same or similar times using suitable techniques, such as extrusion, co-extrusion, interrupted layer co-extrusion (ILC), or the like. In some other embodiments, one or more layers, for example the inner layer 34 and the reinforcing layer 31, can be formed and/or provided separately, and thereafter additional layers, for example layers 32 and 30, can be formed onto, over, or with the layers 31 and 34 by suitable techniques to form the inner tubular member 24.

The inner tubular member 24 may have a uniform stiffness, or may vary in stiffness along its length. For example, a gradual reduction in stiffness from the proximal end to the distal end thereof may be achieved, depending upon the desired characteristics. The gradual reduction in stiffness may be continuous or may be stepped, and may be achieved, for example, by varying the structure, such as the size, thickness, or other physical aspect of one or more of the layers 30/31/32/34, or for example, by varying the materials used in one or more of the layers 30/31/32/34. Such variability in characteristics and materials can be achieved, for example, by using techniques such as ILC, by fusing together separate extruded tubular segments, or in some cases, varying the characteristics and/or even the very presence or absence of certain structures and/or layers.

The one or more reinforcing layer 31, if present, can be constructed with any suitable materials and structures to impart the desired characteristics to the inner tubular member 24. The reinforcing layer 31 can include one or more support members that can comprise, for example, a braid, a coil, a filament or wire, or series of such structures, or the like, including material and/or structure adapted to provide the desired characteristics. Examples of suitable materials for constructing the reinforcing layer include polymers, metals, or metal alloys such as those discussed above, or the like, or any of a broad variety of other suitable materials.

In some embodiments, the reinforcing layer 31 can be a coil 31. The coil 31 may be formed of an elongated filament (e.g., wire, ribbon, or the like) having appropriate dimensions and shape to achieve the desired torque, flexibility, and/or other characteristic. For example, the filament used to form the coil 31 may be circular or non-circular. For instance, the filament may be flattened, ribbon, oval, rectangular, square, triangular, trapezoidal, polygonal, and the like, or any other suitable shape. In describing the filament as being a suitable shape, such as rectangular, square, triangular, or the like, it is the intention not to limit the filament to having a true rectangular, square, triangular, etc., shape. The intention is to include shapes that resemble such shapes. For example, the filament may have rounded corners, nonlinear sides, and/or non-characteristic angles. The coil 31 can be wrapped in a helical fashion by conventional winding techniques. The pitch of adjacent turns of coil 31 may be tightly wrapped so that each turn touches the succeeding turn, or the pitch may be set such that coil 31 is wrapped in an open fashion maintaining a gap between successive turns. The pitch can be constant throughout the length of the coil 31, or can vary, depending upon the desired characteristics, for example flexibility. For example, in some embodiments, the coil 31 can include a distal portion including a relatively open pitch, and a proximal portion having a relatively more closed pitch, such that the coil is more flexible in the distal portion than in the proximal portion. The reinforcing layer 31 may extend the entire length of the inner tubular member 24, or may extend only along a portion of the length thereof. In some embodiments, the reinforcing layer 31 may extend from a point distal of the proximal end to the distal end of the inner tubular member 24. In another embodiment, the reinforcing layer 31 may extend from the proximal end to a point proximal of the distal end of the inner tubular member 24. In still another embodiment, the reinforcing layer 31 may extend from a point distal of the proximal end to a point proximal of the distal end.

One embodiment of the reinforcing layer 31 may be more clearly described herein. Referring to FIG. 4A, reinforcing layer 31 may be a continuous wire 75. A continuous wire is a single filament that extends from one end of the wire to the opposite end of the wire without splicing, welding, brazing or other means of joining two wires together. A continuous wire 75 may overcome challenges associated with initiating and/or terminating a reinforcement member at a location other than the proximal region or distal region of a catheter construction. Using two or more discrete coil sections to achieve dissimilar flexibilities throughout the length of a shaft may be disadvantageous. Terminating and initiating adjacent coil sections at an intermediate location may encourage kinking of the shaft, may allow separation of a reinforcing layer from an inner/outer member, or may create an uneven transition through the shaft, for example.

Continuous wire 75 may be helically wound about at least a portion of inner member 24. Continuous wire 75 may be helically wound at a constant pitch about a portion of inner member 24, or the pitch of continuous wire 75 may be varied step-wise or gradually along a portion of inner member 24. For instance, continuous wire 75 may be tightly wound (i.e., successive turns are placed closer together) along a proximal portion 80 of inner member 24 and continuous wire 75 may be more loosely wound (i.e., successive turns are spaced farther apart) along a distal portion 82 of inner member 24. Continuous wire 75 may be wound from the proximal end of inner member 24 to the distal end of inner member 24 or any portion thereof. For example, continuous wire 75 may be wound from a point distal of the proximal end of inner member 24 to the distal end of inner member 24, continuous wire 75 may be wound from the proximal end of inner member 24 to a point proximal of the distal end of inner member 24, or continuous wire 75 may be wound from a point distal of the proximal end of inner member 24 to a point proximal of the distal end of inner member 24.

As shown in FIG. 4A, inner member 24 may have a lumen 15 extending therethrough. However, in some embodiments, such as a guidewire, inner member 24 may be a core wire not including a lumen, such as lumen 15. Lumen 15, if present, may be sized to provide access to the distal end of the elongate shaft through lumen 15, for example, to accommodate advancing an additional medical device therethrough.

Continuous wire 75 may include a first portion 77, a second portion 79, and a transition region 78 located between first portion 77 and second portion 79. Although continuous wire 75 is shown with one transition region 78, one or more additional transition regions may be included in continuous wire 75. Transition region 78 may provide a transition between first portion 77 and second portion 79. Transition region 78 may include a tapered transition, a step-wise transition, or other such transition between first portion 77 and second portion 79. For example, transition region 78 may alternatively be a region of rotation of continuous wire 75. Continuous wire 75 having different transverse dimensions may be rotated, for instance by 45, 90, or 180 degrees, through transition region 78 in order to vary the flexibility of continuous wire 75. For example, continuous wire 75 may be flattened, rectangular, or otherwise have different transverse dimensions, wherein one of two shorter sides is in contact with the inner member 24 in the proximal portion 80 of inner member 24. In transition region 78, continuous wire 75 may be rotated 90 degrees such that one of two longer sides is in contact with the inner member 24 in the distal portion 82 of inner member 24. By rotating the continuous wire 75, the radial extent of the continuous wire 75 from the longitudinal axis x of the elongate shaft is changed between the proximal portion 80 and the distal portion 82 of inner member 24. The radial extent of the continuous wire 75 is intended to mean the distance from the longitudinal axis x of the elongate shaft to the outermost point of the helically wound continuous wire 75 in a radial direction. As shown in FIG. 4A, the radial extent $R_1$ of the first portion 77 of continuous wire 75 is greater than the radial extent $R_2$ of the second portion 79 of continuous wire 75. Continuous wires 75 of other shapes having different transverse dimensions may be rotated in a similar manner in order to achieve two or more regions of different flexibility. By reducing the radial extent of the continuous wire 75 in the distal portion 82 of the inner member 24, the flexibility of the distal portion 82 is increased. Thus, the second portion 79 of continuous wire 75 having a reduced radial extent may provide a distal tip portion of the shaft with a higher degree of flexibility and a lower profile than a portion of the shaft proximal of the transition region 78.

As can be better seen in FIG. 4B, a first portion 77 of continuous wire 75 may have a first cross-sectional profile having a first cross-sectional area, and a second portion 79 of continuous wire 75 may have a second cross-sectional profile having a second cross-sectional area. The first cross-sectional profile may be constant throughout the first portion 77 of continuous wire 75 and the second cross-sectional profile may be constant throughout the second portion 79 of continuous wire 75. Transition region 78 (FIG. 4A) may provide transition between the cross-sectional profile of the first portion 77 and the cross-sectional profile of the second portion 79 of continuous wire 75. The first cross-sectional profile may be dissimilar from the second cross-sectional profile. For example, the first portion 77 may have a circular cross-sectional profile and the second portion 79 may have a noncircular cross-sectional profile, such as a ribbon, oval, flattened, square, or rectangular profile. The cross-sectional area of the circular cross-sectional profile may or may not be different from the cross-sectional area of the non-circular cross-sectional profile. In other embodiments, the first portion 77 may have a circular or non-circular cross-sectional profile having a first cross-sectional area and the second portion 79 may have a circular or noncircular cross-sectional profile having a second cross-sectional area different from the first cross-sectional area. For example, continuous wire 75 may include a proximal portion 77 having a first circular cross-sectional profile and a distal portion 79 having a second circular cross-sectional profile. The cross-sectional area of the first circular cross-sectional profile may be different from the cross-sectional area of the second circular cross-sectional profile. For instance, the first cross-sectional area may be greater than or less than the second cross-sectional area. Differences in the cross-sectional profile and/or cross-sectional area of the proximal portion relative to the cross-sectional profile and/or cross-sectional area of the distal portion 79 may enhance the flexibility characteristics of the elongate shaft. For example, the distal portion 79 having a dissimilar profile may provide the elongate shaft with a very flexible, lower profile distal tip portion.

Proximal portion 77 of continuous wire 75 may be helically wound around a length of inner member 24. For instance, helically wound proximal portion 77 may extend a majority of the length of inner member 24. In some embodiments, helically wound proximal portion 77 may extend a length of about 20 cm or more, about 50 cm or more, about 75 cm or more, or about 100 cm or more, for example. Distal portion 79 of continuous wire 75 may be helically wound around a length of inner member 24. For instance, helically wound distal portion 79 may extend proximally along inner member 24 from the distal end of inner member 24, or helically wound distal portion 79 may extend distally from the proximal end of distal tip portion 28 to a point within distal tip portion 28. In some embodiments, distal portion 79 may extend for a length of about 5 cm or less, about 3 cm or less, about 2 cm or less, about 1.5 cm or less, or about 1 cm or less along a distal portion of inner member 24, for example. Distal portion 79 may be positioned within a distal tip portion 28 of the shaft.

As mentioned previously, the radial extent $R_1$ of the proximal portion 77 of the helically wound continuous wire 75 along proximal portion 80 of inner member 24 may be greater than the radial extent $R_2$ of the distal portion 79 of the helically wound continuous wire 75 along distal portion 82 of inner member 24. Therefore, the portion of the shaft including the distal portion 79 of continuous wire 75 may have a lower profile and/or a higher degree of flexibility than the portion of the shaft including the proximal portion 77. Additionally or alternatively, a change in the flexibility of the shaft may be achieved by varying the pitch of the continuous wire 75 between the proximal portion 77 and the distal portion 79.

As shown in FIG. 4B, an outer tubular member 26 may be disposed about at least a portion of inner member 24 including the continuous wire 75. Outer tubular member 26 may be disposed about a proximal portion of inner member 24 including the continuous wire 75. For reasons of clarity, an additional layer(s) overlaying continuous wire 75 and disposed within the lumen of outer tubular member 26 as shown in FIG. 3 is not illustrated in FIG. 4B. However, some embodiments may include at least one layer of inner member 24 or an additional layer interposed between continuous wire 75 and outer tubular member 26, or along a portion thereof. In some embodiments, no additional layer may be located between continuous wire 75 and outer tubular member 26.

Distal end 39 of outer tubular member 26 may be located proximate transition region 78. For example, distal end 39 may be positioned about 2 cm or less, about 1 cm or less, or about 0.5 cm or less from transition region 78 of continuous wire 75. Outer tubular member 26 may extend proximally from a point proximate transition region 78 to the proximal region of the elongate shaft. In some embodiments, outer tubular member 26 may extend over the entire proximal portion 77 of helically wound continuous wire 75. In some embodiments, outer tubular member 26 may extend from the proximal end of the elongate shaft to the transition region 78. However, outer tubular member 26 may extend distal of the transition region in some embodiments and may extend to the distal end of the elongate shaft in some embodiments. Outer tubular member 26 may include a plurality of slots or apertures 44 cut through the wall of outer tubular member 26 to provide a degree of flexibility to the elongate shaft. In a preferred embodiment, the outer tubular member has a generally constant diameter over a substantial portion of its length. Thus, the inside surface does not conform to or fill the spaces between successive turns of the reinforcing layer. Outer tubular member 26 will be further described hereinafter.

A distal tip portion 28 may be disposed about a distal portion of inner member 24 including the continuous wire 75. Proximal end 29 of distal tip 28 may be located proximate transition region 78 such that proximal end 29 of distal tip 28 may abut or mate with distal end 39 of outer tubular member 26. For example, proximal end 29 may be positioned about 2 cm or less, about 1 cm or less, or about 0.5 cm or less from transition region 78 of continuous wire 75. In some embodiments, distal tip 28 may extend over and surround a distal portion of outer tubular member 26. Distal tip 28 may extend to the distal end of the elongate shaft to provide a flexible atraumatic tip to the elongate shaft.

Figure 5A:
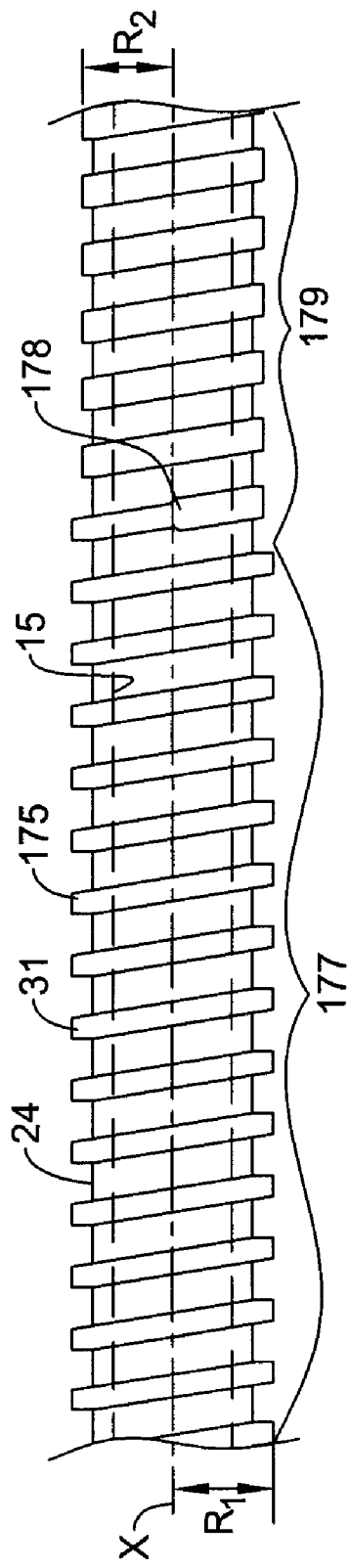
FIG. 5A is a plan view of a portion of the medical device of FIG. 1 with any layers overlaying a reinforcing layer removed, thus exposing an alternative continuous reinforcement member helically wound about a portion of an inner elongate member of the shaft.
Figure 5B:
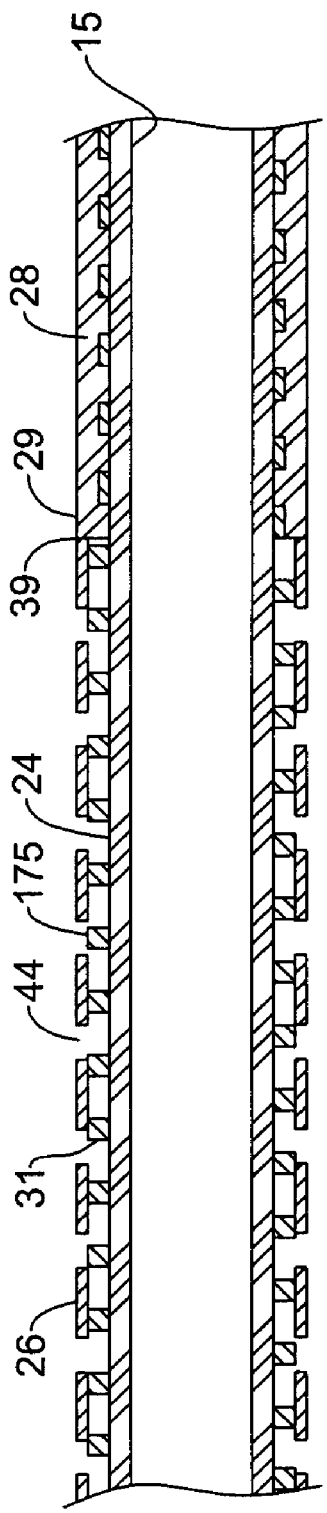
FIG. 5B is a partial cross-sectional view of the portion of the medical device shown in FIG. 5A and including additional tubular members overlaying the continuous reinforcement member.

Another embodiment of reinforcing layer 31 comprising a continuous wire 175 disposed about at least a portion of inner member 24 is shown in FIGS. 5A and 5B. Continuous wire 175 may be similar to continuous wire 75 shown in FIGS. 4A and 4B. Continuous wire 175 may include a proximal portion 177 having first cross-sectional profile and a distal portion 179 having a second cross-sectional profile different from the first cross-sectional profile. A transition region 178 may be located between the proximal portion 177 and the distal portion 179 providing a transition between the two portions of continuous wire 175. The first cross-sectional profile may be a flattened wire (i.e., ribbon) having a first radial extent $R_1$ and the second cross-sectional profile may be a flattened wire (i.e., ribbon) having a second radial extent $R_2$ less than the first radial extent $R_1$. The radial extent of the continuous wire 175 is intended to mean the distance from the longitudinal axis x of the elongate shaft to the outermost point of the helically wound continuous wire 175 in a radial direction. The distal portion 179 having a reduced radial extent may provide the distal tip region of the shaft with a higher degree of flexibility and a lower profile segment than more proximal segments.

As shown in FIG. 5B, an outer tubular member 26 may be disposed about a proximal portion of inner member 24 including the continuous wire 175. As mentioned above, an additional layer(s) may or may not be interposed between outer tubular member 26 and continuous wire 175. Distal end 39 of outer tubular member 26 may be located proximate transition region 178. For example, distal end 39 may be positioned about 2 cm or less, about 1 cm or less, or about 0.5 cm or less from transition region 178 of continuous wire 175. In some embodiments, outer tubular member 26 may extend over transition region 178 and/or distal portion 179 of continuous wire 175. Outer tubular member 26 may include a plurality of slots or apertures 44 cut through the wall of outer tubular member 26 to provide a degree of flexibility to the elongate shaft. Outer tubular member 26 will be further described hereinafter.

A distal tip portion 28 may be disposed about a distal portion of inner tubular member 24 including the continuous wire 175. Proximal end 29 of distal tip 28 may be located proximate transition region 178 such that proximal end 29 of distal tip 28 may abut or adjoin distal end 39 of outer tubular member 26. For example, proximal end 29 may be positioned about 2 cm or less, about 1 cm or less, or about 0.5 cm or less from transition region 178 of continuous wire 175. Distal tip 28 may extend to the distal end of the elongate shaft to provide a flexible atraumatic tip to the elongate shaft.

Figure 6:
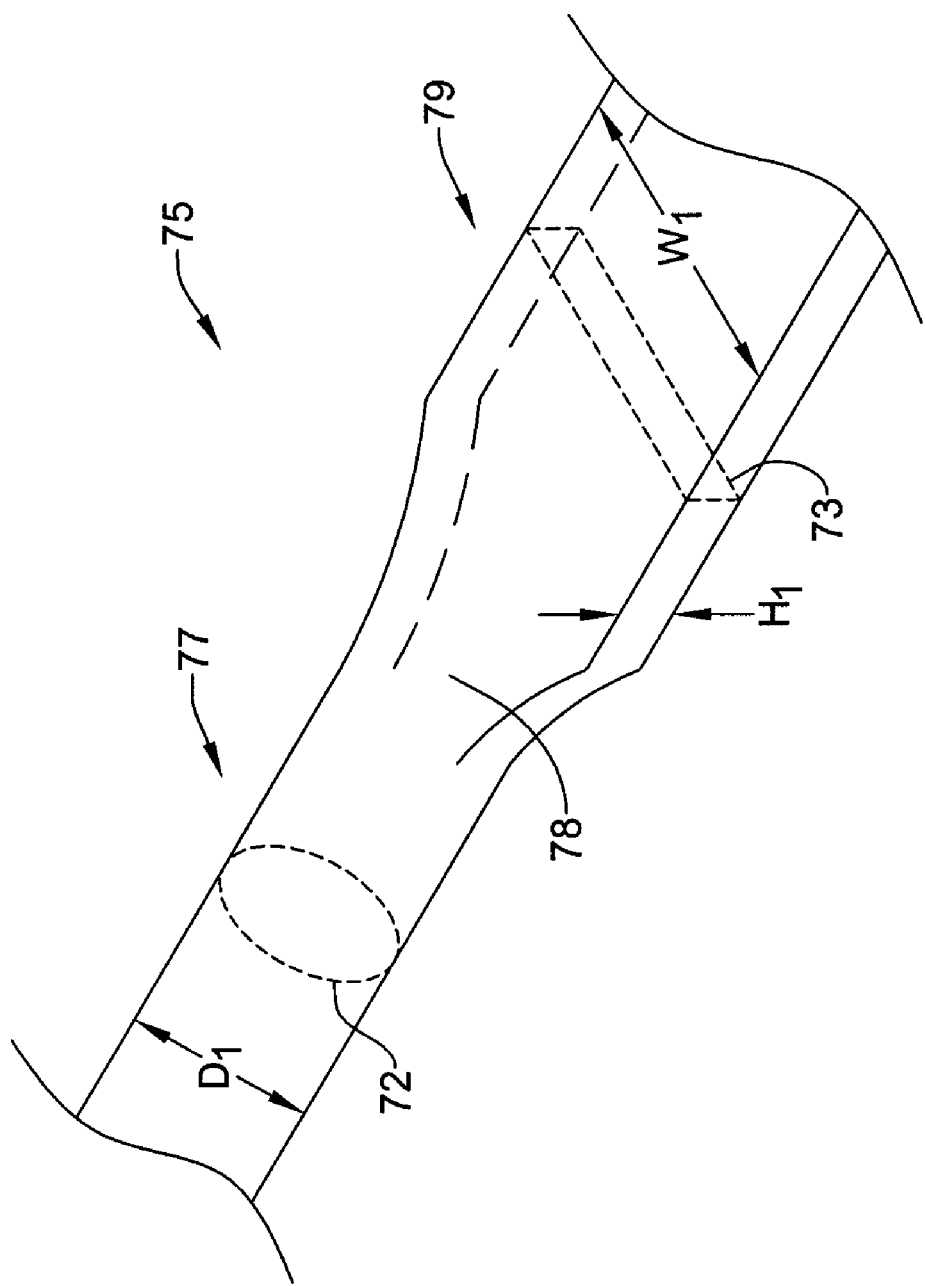
FIG. 6 is a perspective view of a portion of a continuous reinforcement member including a transition region in accordance with the invention as shown in FIGS. 4A and 4B.

FIG. 6 shows a portion of continuous wire 75 including a transition region 78 located between a proximal portion 77 and a distal portion 79 of continuous wire 75 as disclosed regarding FIGS. 4A and 4B. Proximal portion 77 may have a circular cross-sectional profile 72 having a diameter $D_1$ and distal portion 79 may have a non-circular cross-sectional profile 73, which may be a profile having a width $W_1$ and a height $H_1$. Width $W_1$ may be greater than height $H_1$. For example, width $W_1$ may be two times, four times, or ten times greater than height $H_1$. Additionally, diameter $D_1$ may be greater than $H_1$ such that when continuous wire 75 is helically wound about inner member 24, the radial extent $R_1$ of the proximal portion 77 is greater than the radial extent $R_2$ of the distal portion 79. In some embodiments, the cross-sectional area of the cross-sectional profile 72 may be equivalent to the cross-sectional area of the cross-sectional profile 73. In alternative embodiments, the cross-sectional area of profile 72 may be greater than or less than the cross-sectional area of profile 73.

Distal portion 79 may be formed in continuous wire 75 by grinding, cold working, drawing, pressing, shaping, chemical etching, electro-polishing, or otherwise deforming/altering distal portion 79 of continuous wire 75 into the second cross-sectional profile 73. In deforming/altering distal portion 79, transition region 78 is formed, providing a transition between proximal portion 77 and distal portion 79. Distal portion 79 may have a specified length such that when distal portion 79 is helically wound around inner member 24, distal portion 79 extends along inner member 24 a length of about 0.5 cm to about 5 cm, or about 1 cm to about 3 cm or about 1 cm to about 1.5 cm, for example. Thus, the chosen length of distal portion 79 may be a function of the outer diameter of inner member 24, the pitch of helically wound continuous wire 75, and/or the number of windings of continuous wire 75, for example.

Proximal portion 77 may have a specified length such that when proximal portion 77 is helically wound around inner member 24, proximal portion 77 extends a majority of the length of the inner member 24. In some embodiments, proximal portion 77 may have a length such that helically wound proximal portion 77 extends about 20 cm or more, about 50 cm or more, or about 100 cm or more, for example. Helically wound proximal portion 77 may be sized to extend within about 10 cm or less, about 5 cm or less, about 2 cm or less, or about 1 cm or less of the proximal end of inner member 24, for example. Thus, the chosen length of proximal portion 77 may be a function of the outer diameter of inner member 24, the pitch of helically wound continuous wire 75, and/or the number of windings of continuous wire 75, for example.

Figure 7:
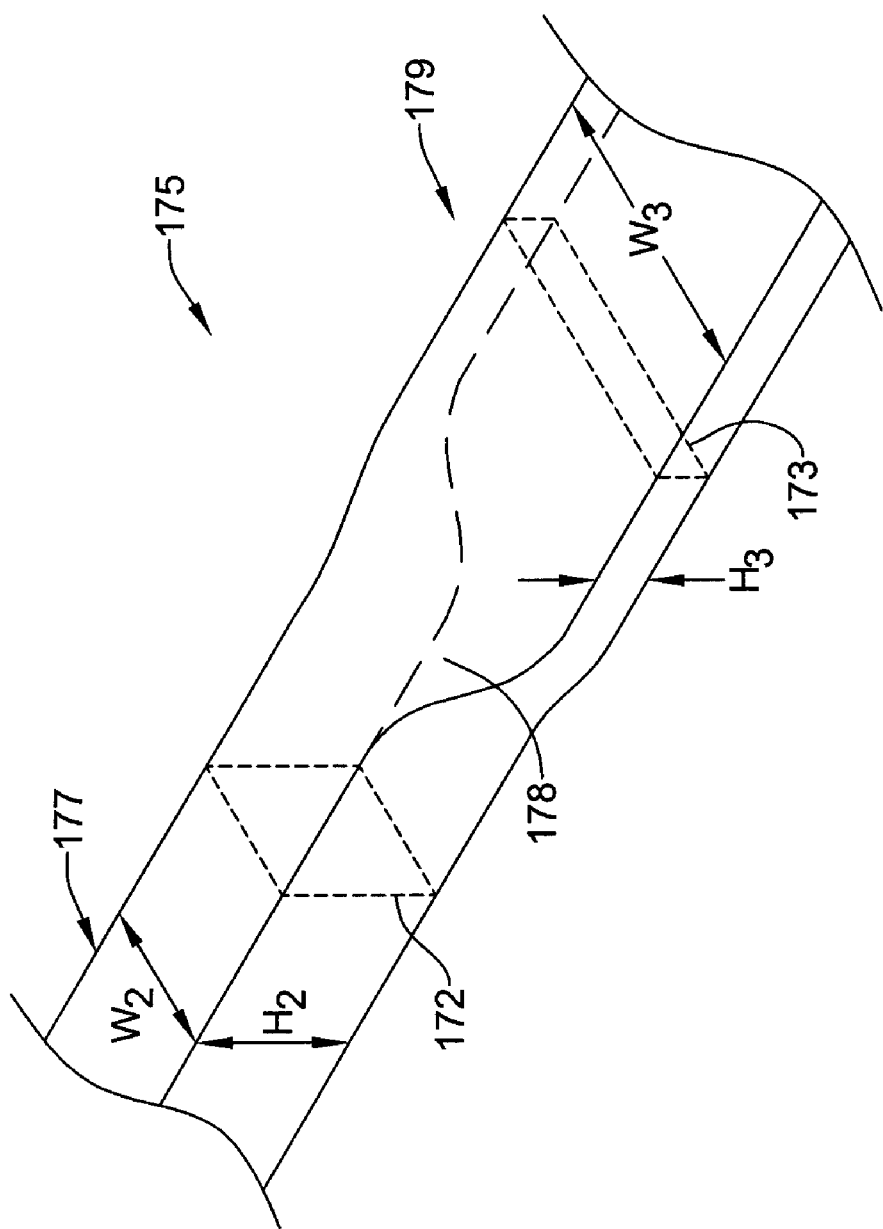
FIG. 7 is a perspective view of a portion of a continuous reinforcement member including a transition region in accordance with the invention as shown in FIGS. 5A and 5B.

FIG. 7 shows a transition region 178 located between a proximal portion 177 and a distal portion 179 of continuous wire 175 as disclosed regarding FIGS. 5A and 5B. Proximal portion 177 may have a non-circular cross-sectional profile 172, which may be a ribbon profile having a width $W_2$ and a height $H_2$. Width $W_2$ and height $H_2$ may be different, thus cross-sectional profile 172 may be substantially rectangular (e.g., flat wire), or width $W_2$ and height $H_2$ may be substantially equivalent, thus cross-sectional profile 172 may be substantially square (e.g., flat wire). In describing the cross-sectional profile as square or rectangular, profiles are intended to resemble those of squares and rectangles. For example, the cross-sectional profiles may include rounded corners, nonlinear sides, and/or non-characteristic angles, thus not creating a true square or rectangular profile. Distal portion 179 may have a non-circular cross-sectional profile 173, which may be a ribbon profile having a width $W_3$ and a height $H_3$. Width $W_3$ may be greater than height $H_3$, such that distal portion 179 of continuous wire 175 is a flattened ribbon portion. In some embodiments, width $W_3$ may be greater than width $W_2$ and/or height $H_2$ may be greater than height $H_3$. For example, width $W_3$ may be two times, four times, or ten times greater than width $W_2$ and/or height $H_2$ may be two times, four times, or ten times greater than height $H_3$. $H_2$ may be greater than $H_3$ such that the radial extent $R_1$ of the proximal portion 177 is greater than the radial extent $R_2$ of the distal portion 179 when the continuous wire 175 is helically wound around inner member 24. In some embodiments, the cross-sectional area of the first cross-sectional profile 172 may be equivalent to the cross-sectional area of the second cross-sectional profile 173. In alternative embodiments, the first cross-sectional area of profile 172 may be greater than or less than the second cross-sectional area of profile 173.

Similar to continuous wire 75, distal portion 179 may be formed in continuous wire 175 by grinding, cold working, drawing, pressing, shaping, chemical etching, electro-polishing, or otherwise deforming/altering distal portion 179 of continuous wire 175 into the second cross-sectional profile 173. In deforming/altering distal portion 179, transition region 178 is formed providing a transition between proximal portion 177 and distal portion 179. Distal portion 179 may have a specified length such that when distal portion 179 is helically wound around inner member 24, distal portion 179 extends along inner member 24 a length of about 0.5 cm to about 5 cm, or about 1 cm to about 3 cm or about 1 cm to about 1.5 cm, for example. Thus, the chosen length of distal portion 179 may be a function of the outer diameter of inner member 24, the pitch of helically wound continuous wire 175, and/or the number of windings of continuous wire 175, for example.

Proximal portion 177 may have a specified length such that when proximal portion 177 is helically wound around inner member 24, proximal portion 177 extends a majority of the length of the inner member 24. In some embodiments, proximal portion 177 may have a length such that helically wound proximal portion 177 extends about 20 cm or more, about 50 cm or more, or about 100 cm or more, for example. Helically wound proximal portion 177 may be sized to extend within about 10 cm or less, about 5 cm or less, about 2 cm or less, or about 1 cm or less of the proximal end of inner member 24, for example. Thus, the chosen length of proximal portion 177 may be a function of the outer diameter of inner member 24, the pitch of helically wound continuous wire 175, and/or the number of windings of continuous wire 175, for example.

Referring again to FIGS. 1-3, the outer member 26 can also be a generally tubular member including a proximal region 36 having a proximal end 37 and a distal region 38 having a distal end 39. The outer tubular member 26 can be disposed about at least a portion of the inner tubular member 24 at a location along the length of the shaft 12 between proximal end 18 and distal end 22. In the embodiment shown, the outer member 26 is disposed about the inner tubular member 24 along the proximal portion 16 of the shaft 12, but it should be understood that other locations are possible.

The length of the outer tubular member 26 can also vary, depending upon, for example, the length of the shaft 12, the desired characteristics and functions of the catheter 10, and other such parameters. In some embodiments, the outer member 26 has a length that allows it to be disposed over the majority of the length of the inner tubular member 24, and in some embodiments, is disposed about all but up to the distal most 15 cm or less of the inner tubular member 24 and/or all but the proximal most 15 cm or less of the inner tubular member 24. In some embodiments, the distal end of the outer tubular member 26 is disposed about 3.0 cm or less, 2.0 cm or less, 1.5 cm or less or 1.0 cm or less proximal the distal end of the inner member 24. In some embodiments, the length of the outer tubular member 26 can be in the range of about 1 cm to about 299 cm or more, or in some embodiments in the range of about 19 cm-249 cm.

The tubular outer member 26 defines a lumen 40 that can be adapted and/or configured to house or surround a portion of the inner tubular member 24. In some embodiments, the lumen 40 can have an inner diameter that is in the range of about 0.015 inch to about 0.06 inch in size, and in some embodiments, in the range of about 0.02 inch to about 0.035 inch in size. In some embodiments, the outer tubular member 26 can have an outer diameter that is in the range of about 0.016 inch to about 0.07 inch in size, or in the range of about 0.02 inch to about 0.04 inch in size. It should be understood however, that these, and other dimensions provided herein, are by way of example only.

In at least some embodiments, the outer tubular member 26 can have an inner diameter that is greater than the outer diameter of the inner tubular member 24. As such, the outer tubular member 26 can be disposed about the inner tubular member 24 (i.e., a portion of the inner tubular member 24 is disposed within the lumen 40 of the outer member) such that a space or gap 42 is defined between at least a portion of the outer surface 25 of the inner tubular member 24 and the inner surface 27 of the outer member 26. In some embodiments, the space or gap 42 can be in the range of about 0.0002 to about 0.004 inch in size, and in some embodiments, in the range of about 0.0005 to about 0.003 inch in size. Again, it should be understood that these dimensions are provided by way of example only. In some embodiments, space or gap 42 may be substantially filled by reinforcing layer 31. For example, continuous wire 75 may be disposed in gap 42 between inner member 24 and outer tubular member 26. However, in some embodiments the outer tubular member 26 is substantially contiguous with the inner tubular member 24 such that no gap or space is formed between the inner tubular member 24 and the outer tubular member 26.

Typically, relatively large portions of the gap or space 42 remain open or unfilled by any other structure of the catheter 10 along a substantial portion of the length thereof, and in some cases along a substantial portion of the length of the outer tubular member 26. For example, in some embodiments, 50% or more, 75% or more, 90% or more, or 95% or more of the gap or space 42 remains open and/or unfilled by any other structure of the catheter.

In some embodiments, attachment points along the length of the outer tubular member 26 may be used to attach to the inner tubular member 24. As a result, the gap or space 42 may be partially or totally filled at these attachment points, and as such, divided up into what may be considered multiple and/or a plurality of separate gaps or spaces that are unfilled. Additionally, other structures, such as coils, bands, braids, polymer layers, or the like, may fill portions of the gap or space 42. Even so, such multiples of the gap or space 42, or the so defined multiple gaps or spaces 42 may still collectively extend along a substantial portion of the length of the outer tubular member 26 and remain overall substantially unfilled over the majority of the length thereof, for example, in percentages of the total length as given above. As such, the outer tubular member 26 can act to reinforce or impart desired properties, such as torsional and lateral rigidity, to the catheter shaft 12, and may allow at least the portion of the inner tubular member 24 surrounded by the gap or space 42 to be separate from, and in some cases bend and/or move laterally within, the lumen 40. Some examples of structure, methods, and techniques of coupling the tubular outer member 26 to the inner tubular member 24 will be discussed in more detail below.

The outer tubular member 26 can be adapted and/or configured to have a desired level of stiffness, torqueability, flexibility, and/or other characteristics. Those of skill in the art and others will recognize that the dimensions, structure, and materials of the outer tubular member 26 are dictated primarily by the desired characteristics, and the function of the final catheter 10, and that any of a broad range of the dimensions, structure, and materials can be used.

The desired stiffness, torqueability, lateral flexibility, bendability or other such characteristics of the outer member 26 can be imparted or enhanced by the structure of the outer tubular member 26. For example, the outer tubular member 26 may include a thin wall tubular structure, including one or a plurality of apertures 44, such as grooves, cuts, slits, slots, or the like, formed in a portion of, or along the entire length of, the tubular outer member 26. Such structure may be desirable because it may allow outer tubular member 26, or portions thereof, to have a desired level of lateral flexibility as well as have the ability to transmit torque and pushing forces from the proximal region 36 to the distal region 38. In some embodiments, slots or apertures 44 may extend substantially transverse to the longitudinal axis x of the outer tubular member 26. The apertures 44 can be formed in essentially any known way. For example, apertures 44 can be formed by methods such as micro-machining, saw-cutting, laser cutting, grinding, milling, casting, molding, chemically etching or treating, or other known methods, and the like. In some such embodiments, the structure of the outer tubular member 26 is formed by cutting and/or removing portions of the tube to form apertures 44.

In some embodiments, the apertures 44 can completely penetrate the outer tubular member 26 such that there is fluid communication between the lumen 40 and the exterior of the outer tubular member 26 through the apertures 44. In some embodiments, the apertures 44 may only partially extend into the structure of the outer tubular member 26, either on the interior or exterior surface thereof. Some other embodiments may include combinations of both complete and partial apertures 44 through the structure of the outer tubular member 26. The shape and size of the apertures 44 can vary, for example, to achieve the desired characteristics. For example, the shape of apertures 44 can vary to include essentially any appropriate shape, such as square, round, rectangular, pill-shaped, oval, polygonal, elongate, irregular, or the like, and may include rounded or squared edges, and can be variable in length and width, and the like.

Additionally, the spacing, arrangement, and/or orientation of the apertures 44, or in some embodiments, associated spines or beams that may be formed, can be varied to achieve the desired characteristics. For example, the number or density of the apertures 44 along the length of the outer tubular member 26 may be constant or may vary, depending upon the desired characteristics. For example, the number or proximity of apertures 44 to one another near one end of the outer member 26 may be high, while the number or proximity of slots to one another near the other end of the outer tubular member 26 may be relatively low and/or non existent, or vice versa. For example, in the embodiment shown in FIGS. 1, 2, and 3, the distal region 38 of the outer tubular member 26 includes a plurality of apertures 44 having a relatively high density relative to the plurality of apertures 44 located in the proximal region 36. As such, the distal region 38 can have a greater degree of lateral flexibility relative to the proximal region 36. The density of the apertures 44 can vary gradually or in a stepwise fashion over the length of the outer tubular member. And as suggested above, certain portions of the outer tubular member 26 may not include any such apertures.

In some embodiments, the distal about 10% to about 50% of the total length of the outer tubular member 26 can include apertures 44 defined therein at a relatively high density, while the proximal about 50% to about 90% of the total length of the outer tubular member 26 include apertures 44 defined therein at a relatively low density, and/or is free of such apertures 44. For example, in some embodiments, the distal region 38 having a length in the range of about 30 cm to about 70 cm includes apertures 44 defined therein at a relatively high density to provide for relatively greater flexibility, while the remaining length in the proximal region 36 of the outer tubular member 26 include apertures 44 defined therein at a relatively low density, and/or is free of such apertures 44, to provide for relatively greater stiffness. It should be understood however, that these, and other dimensions provided herein, are by way of example embodiments only, and that in other embodiments, the disposition of apertures 44 can vary greatly from the dimensions given, depending upon the desired characteristics and function of the device.

As suggested above, the apertures 44 may be formed such that one or more spines or beams 50 are formed in the tubular outer member 26. Such spines or beams 50 (FIG. 1) could include portions of the tubular member 26 that remain after the apertures 44 are formed in the body of the outer tubular member 26. Such spines or beams 50 may act to maintain a relatively high degree of torsional stiffness, while maintaining a desired level of lateral flexibility. In some embodiments, some adjacent apertures 44 can be formed such that they include portions that overlap with each other about the circumference of the tube. In other embodiments, some adjacent apertures 44 can be disposed such that they do not necessarily overlap with each other, but are disposed in a pattern that provides the desired degree of lateral flexibility. Additionally, the apertures 44 can be arranged along the length of, or about the circumference of, the outer tubular member 26 to achieve desired properties. For example, the apertures 44 can be arranged in a symmetrical pattern, such as being disposed essentially equally on opposite sides about the circumference of the outer tubular member 26, or equally spaced along the length of the outer tubular member, or can be arranged in an increasing or decreasing density pattern, or can be arranged in a non-symmetric or irregular pattern.

Collectively, these Figures and this Description illustrate that changes in the arrangement, number, and configuration of slots may vary without departing from the scope of the invention. Some additional examples of shaft constructions and/or arrangements of cuts or slots formed in a tubular body are disclosed in U.S. Pat. No. 6,428,489 and in published U.S. patent application Ser. No. 09/746,738 (Pub. No. US 2002/0013540), and Ser. No. 10/400,750 (Pub. No. US-2004/0193140), all of which are incorporated herein by reference. Also, some additional examples of shaft constructions and/or arrangements of cuts or slots formed in a tubular body for use in a medical device are disclosed in U.S. patent application Ser. Nos. 10/375,493, and 10/400,750, which are also incorporated herein by reference.

In addition to, in combination with, or as an alternative to the structure of the outer member 26, the materials selected for outer tubular member 26 may also be chosen so that may have the desired characteristics. The outer tubular member 26 may be formed of any materials suitable for use, dependent upon the desired properties of the catheter 10. For example, outer tubular member 26 may be formed of materials having a desired modulus of elasticity, given the structure used. Some examples of suitable materials include metals, metal alloys, polymers, or the like, or combinations or mixtures thereof.

Some examples of suitable metals and metal alloys include stainless steel, such as 304V, 304L, and 316L stainless steel; alloys including nickel-titanium alloy such as linear elastic or superelastic (i.e., pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. In some embodiments, it is desirable to use metals, or metal alloys that are suitable for metal joining techniques such as welding, soldering, brazing, crimping, friction fitting, adhesive bonding, etc.

Some examples of suitable polymeric materials may include, but are not limited to: poly(L-lactide) (PLLA), poly (D,L-lactide) (PLA), polyglycolide (PGA), poly(L-lactide-co-D,L-lactide) (PLLA/PLA), poly(L-lactide-co-glycolide) (PLLA/PGA), poly(D, L-lactide-co-glycolide) (PLA/PGA), poly(glycolide-co-trimethylene carbonate) (PGA/PTMC), polyethylene oxide (PEO), polydioxanone (PDS), polycaprolactone (PCL), polyhydroxylbutyrate (PHBT), poly(phosphazene), polyD,L-lactide-co-caprolactone) (PLA/PCL), poly (glycolide-co-caprolactone) (PGA/PCL), polyanhydrides (PAN), poly(ortho esters), poly(phoshate ester), poly(amino acid), poly(hydroxy butyrate), polyacrylate, polyacrylamid, poly(hydroxyethyl methacrylate), polyurethane, polysiloxane and their copolymers, or mixtures or combinations thereof. Some other potentially suitable polymer materials may include those listed above with reference to the inner tubular member 24.

As indicated above, some embodiments may include linear-elastic or super-elastic nitinol in various structures and/or components of the shaft 12 (e.g., outer tubular member 26, inner tubular member 24, etc.). The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 45 to about 60 weight percent nickel, with the remainder being essentially titanium. It should be understood, however, that in other embodiment, the range of weight percent nickel and titanium, and or other trace elements may vary from these ranges. Within the family of commercially available nitinol alloys, are categories designated as "superelastic" (i.e., pseudoelastic) and "linear elastic" which, although similar in chemistry, exhibits distinct and useful mechanical properties.

In some embodiments, a superelastic alloy, for example a superelastic nitinol, can be used to achieve desired properties. Such alloys typically display a substantial "superelastic plateau" or "flag region" in its stress/strain curve. Such alloys can be desirable in some embodiments because a suitable superelastic alloy will provide an outer member 26 that exhibits some enhanced ability, relative to some other non-superelastic materials, of substantially recovering its shape without significant plastic deformation upon the application and release of stress, for example, during placement of the catheter in the body.

In some other embodiments, a linear elastic alloy, for example a linear elastic nitinol, can be used to achieve desired properties. For example, in some embodiments, certain linear elastic nitinol alloys can be generated by the application of cold work, directional stress, and/or heat treatment, such that the material fabricated does not display a substantial "superelastic plateau" or "flag region" in its stress/strain curve. Instead, in such embodiments, as recoverable strain increases, the stress continues to increase in a somewhat linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there are no martensite/austenite phase changes detectable by DSC and DMTA analysis in the range of about −60° C. to about 120° C. The mechanical bending properties of such material are therefore generally inert to the effect of temperature over a broad range of temperature. In some particular embodiments, the mechanical properties of the alloy at ambient or room temperature are substantially the same as the mechanical properties at body temperature. In some embodiments, the use of the linear elastic nickel-titanium alloy allows the outer member to exhibit superior "pushability" around tortuous anatomy. One example of a suitable nickel-titanium alloy exhibiting at least some linear elastic properties is FHP-NT alloy commercially available from Furukawa Techno Material Co. of Kanagawa, Japan. Additionally, some examples of suitable nickel-titanium alloy exhibiting at least some linear elastic properties include those disclosed in U.S. Pat. Nos. 5,238,004 and 6,508,803, which are incorporated herein by reference.

In some embodiments, the outer tubular member 26, or other portions of the shaft 12, can be formed of a shape-memory material, for example a shape memory alloy such as a shape memory nitinol. In such embodiments, the shape memory effect can be used in the deployment or use of the catheter, for example in causing the outer tubular member 26, or other portions of the shaft 12, to move from a first insertion configuration to a second use configuration, or, for example, for the outer tubular member 26 to "remember" its desired shape after deformation to another shape.

For example, in some embodiments, the outer tubular member 26 can include or be made of a shape memory alloy that is martensite at room temperature, and has a final austenite transition temperature ($A_f$) somewhere in the temperature range between room temperature and body temperature. For example, in some such embodiments, the shape memory alloy has a final austenite transition temperature in the range of about 25° C. and about 37° C. (e.g., about body temperature). In some such embodiments, it may be desirable that the final austenite transition temperature be at least slightly below body temperature, to ensure final transition at body temperature. This feature allows the outer member 26 to be inserted into the body of a patient in a martensitic state, and assume its preformed, austenitic shape when exposed to the higher body temperature within the anatomy, or at the target site. In this embodiment, deployment of the outer tubular member 26 can be achieved by a shape memory effect; as the material warms, it undergoes a transition from martensite to austenite form, causing transformation of the outer tubular member 26 from the first configuration to the second configuration.

In other example embodiments, the outer tubular member 26 can include or be made of a shape-memory alloy that could have a transition temperature $M_d$ (wherein $M_d$ highest temperature to strain-induced martensite) that is in the range of body temperature (e.g., about 37° C.) or greater, below which the alloy retains sufficient stress-induced martensitic property to allow placement of the outer tubular member 26 at or above its final austenite transition temperature ($A_f$). In other words, this allows the catheter, including the outer tubular member 26 in its preformed austenitic state, to be inserted and navigated in the anatomy, where the outer tubular member 26 may be exposed to stress that may promote portions thereof to undergo stress-induced martensitic (SIM) transformation. Thereafter, the outer tubular member 26 may recover its preformed, austenitic shape when released from the stress of navigation, at a temperature that may be substantially above the final austenite transition temperature without significant plastic, or otherwise permanent deformation. Additionally, in some such embodiments, the outer tubular member 26 can be constrained, for example, in a delivery device, such as a guide catheter, in a stress-induced martensitic (SIM) state, and recover its preformed, austenitic shape when released from the constraints of the catheter, at a temperature that may be substantially above the final austenite transition temperature without significant plastic, or otherwise permanent deformation. In these embodiments, the final austenite temperature may be quite low, e.g., 4° C. or lower, or it may be up to room temperature or higher.

In yet other embodiments, the outer tubular member 26 can include or be made of a shape memory alloy that is martensite at body temperature, and has a final austenite transition temperature ($A_f$) somewhere in the temperature range above body temperature. This feature allows the catheter including the outer tubular member 26 to be navigated in a martensitic state, and maintain a martensitic state until exposed to a temperature higher than body temperature. The outer tubular member 26 can then be heated to the necessary temperature above body temperature to make the transformation from martensite to austenite using an external heating means or mechanism. Such mechanisms may include the injection of heated fluid through the catheter or other device, the use of electrical or other energy to heat the outer tubular member 26, or other such techniques. In some such embodiments, the shape-memory alloy has a final austenite transition temperature in the range of about 37° C. to about 45° C. It may be desirable that the final austenite transition temperature be at least slightly above body temperature, to ensure there is not final transition at body temperature. Some examples of Nitinol cylindrical tubes having desired transition temperatures, as noted above, can be prepared according to known methods.

Referring to FIG. 3, the outer tubular member 26 may be connected to the inner tubular member 24 using any of a broad variety of suitable techniques, some examples of which may include adhesive bonding, friction fitting, mechanically fitting, crimping, chemically bonding, thermally bonding, welding (e.g., resistance, Rf, or laser welding), soldering, brazing, or the use of a connector member or material, or the like, or combinations thereof. As discussed above, in at least some embodiments, the outer tubular member 26 can be disposed about the inner tubular member 24 (i.e., a portion of the inner tubular member 24 is disposed within the lumen 40 of the outer member) such that a space or gap 42 is defined between at least a portion of the outer surface 25 of the inner tubular member 24 and the inner surface 27 of the outer tubular member 26. In some embodiments, there may be no space between outer tubular member 26 and inner member 24, or space or gap 42 may be substantially filled with another member, such as reinforcement member 31.

In FIG. 3, the outer tubular member 26 is attached to the inner tubular member 24 at one or more proximal attachment point 53, one or more distal attachment point 59, and one or more intermediate attachment point 61. In some embodiments, such attachment points can be achieved, for example, using an adhesive material, for example, a cyanoacrylate, or other suitable type of adhesive. In at least some embodiments, only a relatively small portion of the outer member 26 is connected to the inner tubular member 24 at the attachment points. For example, the length of each individual bond joint, especially at the intermediate bond joints, may only be about 5 cm or less, or 3 cm or less, or 1 cm or less, or 0.5 cm or less. In some embodiments, where appropriate, the bonds extend under or within about five or fewer of the apertures 44, or three or even two or fewer of the apertures 44, along the length of the outer tubular member. Some embodiments may include a plurality of intermediate attachment point 61 spaced apart along the length of the shaft 12. In some embodiments, the distance between attachment points along the length of the shaft 12 may be in the range of about 5 cm and about 40 cm, or in the range of about 7 cm to about 30 cm, and may vary or be constant along the length of the shaft 12. For example, the spacing between attachment points may be closer together near the distal end of the shaft, and may be farther apart near the distal portion of the shaft 12.

As indicated above, the distal portion 20 of the shaft 12 can include a distal tip 28. The distal tip 28 can be a structure, assembly, construction and/or arrangement adapted and/or configured to provide characteristics such as shapability, flexibility, steerability, atraumatic characteristics, or the like, for example, to the distal portion and/or distal end of the shaft 12. A broad variety of distal tip constructions, configurations, and/or structures are generally known for use on medical devices, such as catheters, and may be used. In some embodiments, the distal tip 28 may be disposed at the distal portion 20 of the shaft 12, and may extend distally beyond other portions of the shaft 12. In some embodiments, distal tip 28 may extend proximally from the distal end 22 of shaft 12 to transition region 78 of continuous wire 75. Thus, distal tip 28 may extend over distal portion 79 of continuous wire 75. The low profile of distal portion 79 provides distal tip 28 with a higher degree of flexibility and lower profile than portions of elongate shaft 12 proximal of transition region 78 of continuous wire 75.

In some embodiments, the distal tip 28 is simply one or more portions of the shaft 12, and/or components thereof (e.g. the inner and/or outer tubular members 24/26) that include materials and/or structures to provide the desired characteristics. For example, in the embodiment shown in FIG. 3, the distal tip 28 can include and/or extend about the distal portion 20 of shaft 12 including the inner tubular member 24. In this regard, the distal tip 28 may include the distal portion 20 of shaft 12 including the inner tubular member 24, and may additionally include one or more additional layers and/or structures 52 disposed about the distal portion 20 of shaft 12 including the inner tubular member 24. In other embodiments, however, the distal tip 28 may include structure and/or material that may be considered to be separate and distinct from other portions of the shaft, but that is connected to the distal portion of the shaft 12 to form the distal tip.

In FIG. 3, the layer 52 is disposed about the distal portion 20 of shaft 12 including the inner tubular member 24. The layers 30, 32, and 34 of the inner tubular member 24 may include distal portions, for example 45 and 49, that include materials having desirable flexibility characteristics, for example, as discussed above. Additionally, the layer 52 may be made of or include any suitable material or structure, and may be disposed by any suitable process, the materials, structures, and processes varying with the particular application and characteristics desired. For example, in some embodiments, the one or more additional layers and/or structures may include a layer of polymer or other such material, or structures such as coils, braids, ribbons, wires, bands, or the like.

In this embodiment, the outer layer 52 may include and/or be made of a polymer material disposed about the distal portion 35 of the inner tubular member 24. For example, the outer layer 52 may include a flexible polymer material having a durometer in the range of about 5 D to about 35 D. Some examples of suitable polymers may include those discussed above with regard to the layers of the inner tubular member 24, with one example being a PEBA material, or the like. As can be appreciated, in some embodiments, the coil layer 31, such as distal portion 79 of continuous wire 75, extends partially into the distal tip 28, but ends and is spaced proximally from the distal end 22. In other embodiments, however, the coil 31, or other such reinforcing structure, or the like, may extend to the distal end 22. Additionally, it should be understood that one or more additional layers and/or constructions may be used in the distal tip 28.

The outer layer 52 may be sized appropriately so as to maintain a generally constant diameter in the transition between the outer tubular member 26 and the outer layer 52, and may include a portion 65 that abuts and/or overlaps the distal end 39 of the outer tubular member 26 to provide a smooth transition. Additionally, as in the embodiment shown, the outer tubular member 26 may include a recessed, or reduced diameter portion at the distal end 39 thereof, and the outer layer 52 may overlap and/or mate with the recessed portion to provide for a smooth transition. In other embodiments, however, a tapered or step down transition may be provided.

The outer layer 52 can be constructed and/or disposed using any appropriate technique, for example, by extrusion, co-extrusion, interrupted layer co-extrusion (ILC), coating, heat shrink techniques, heat bonding, thermally bonding, casting, molding, fusing one or several segments of an outer layer material end-to-end, adhesive bonding, chemically bonding, crimping, friction fitting, mechanically fitting, or the like, or combinations thereof.

A lubricious, a hydrophilic, a protective, or other type of coating may be applied over portions of or the entire shaft 12. Hydrophobic coatings such as fluoropolymers provide a dry lubricity which improves catheter handling and device exchanges. Lubricious coatings can aid in insertion and steerability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

It should also be understood that in some embodiments, a degree of MRI compatibility can be imparted into shaft 12. For example, to enhance compatibility with Magnetic Resonance Imaging (MRI) machines, it may be desirable to construct portions of the outer tubular member 26, portions of the inner tubular member 24, or other portions of the shaft 12, in a manner, or use materials, that would impart a degree of MRI compatibility. For example, the lengths of relatively conductive structures within the shaft 12 may be limited to lengths that would not generate undue heat due to resonance waves created in such structures when under the influence of an MRI field generated by an MRI machine. Alternatively or additionally, portions, or the entire shaft 12 may be made of a material that does not substantially distort the image and create substantial artifacts (artifacts are gaps in the image). Certain ferromagnetic materials, for example, may not be suitable because they may create artifacts in an MRI image. Additionally, all or portions of the shaft 12, may also be made of, impregnated with, plated or clad with, or otherwise include a material and/or structure that the MRI machine can image. Some materials that exhibit these characteristics include, for example, tungsten, Elgiloy, MP35N, nitinol, and the like, and others. Additionally, some structures including or made of such materials, such as marker bands, marker coils, rings, impregnated polymer sections, or the like, may be added to or included in the shaft 12. Those skilled in the art will recognize that these materials can vary widely without departing from the spirit of the invention.

Additionally, all or portions of the shaft 12, or components or layers thereof, may be made of, impregnated with, plated or clad with, or otherwise include a radiopaque material and/or structure to facilitate radiographic visualization. Radiopaque materials are understood to be materials capable of producing a relatively bright image on a fluoroscopy screen or another imaging technique during a medical procedure. This relatively bright image may aid the user of catheter 10 in determining its location. Some examples of radiopaque materials can include, but are not limited to, gold, platinum, palladium, tantalum, tungsten alloy, polymer material loaded with radiopaque filler, and the like.

For example, with reference to FIGS. 1-3, the inner tubular member 24 can include one or more radiopaque marker member 55 disposed in the distal portion 35 between the intermediate and outer layers 32/30, or at other positions and/or locations. Additionally, the outer tubular member 26 can include one or more marker members disposed thereon. In the embodiment shown, the marker member 55 is a tubular marker band, but it should be understood that other marker structures and arrangements, such as marker coils, rings, impregnated polymer sections, or the like, may be used, and may be disposed at locations along and/or within the shaft 12. Furthermore, the elongate shaft 12, or portions thereof, may be curved and/or shaped as desired, or be adapted and/or configured to be curved and/or shaped as desired, depending on the particular application.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An elongate medical device, comprising:
    an inner elongate member having a proximal portion and a distal portion;
    a helically wound continuous wire comprising a single filament including a proximal portion having a first cross-sectional profile, a distal portion having a second cross-sectional profile different from the first cross-sectional profile, and a transition region between the first portion and the second portion, the proximal portion of the continuous wire being disposed about the proximal portion of the inner elongate member and the distal portion of the continuous wire being disposed about the distal portion of the inner elongate member;
    an outer tubular member disposed about at least a part of the proximal portion of the inner elongate member and at least a part of the proximal portion of the helically wound continuous wire, the outer tubular member including a wall and a plurality of slots extending through the wall; and
    a distal tip portion extending over and surrounding at least a part of the distal portion of the inner elongate member and at least a part of the distal portion of the helically wound continuous wire.

2. The elongate medical device of claim 1, wherein the distal tip portion includes a proximal end, and the proximal end of the distal tip portion is disposed proximate the transition region.

3. The elongate medical device of claim 1, wherein the distal tip portion has a proximal end and the outer tubular member has a distal end, wherein the proximal end of the distal tip portion abuts the distal end of the outer tubular member.

4. The elongate medical device of claim 1, wherein the distal tip portion and the outer tubular member have generally equal outer diameters.

5. The elongate medical device of claim 1, wherein the first cross-sectional profile is circular, and wherein the second cross-sectional profile is rectangular.

6. The elongate medical device of claim 1, wherein the first cross-sectional profile and the second cross-sectional profile are both generally rectangular and are differently sized.

7. The elongate medical device of claim 1, wherein the first cross-sectional profile and the second cross-sectional profile have different cross-sectional areas.

8. The elongate medical device of claim 1, wherein the first cross-sectional profile has a cross-sectional area greater than that of the second cross-sectional profile.

9. The elongate medical device of claim 1, wherein the proximal portion of the helically wound continuous wire extends over a majority of the length of the inner elongate member.

10. An elongate medical device, comprising:
    an inner elongate tubular member having a proximal portion and a distal portion;
    a helically wound coil comprising a single filament, the single filament including a proximal portion having a proximal cross-sectional profile, a distal portion having a distal cross-sectional profile different from the proximal cross-sectional profile, and a transition region between the proximal portion and the distal portion, the continuous helical wire being disposed about the inner elongate tubular member such that the proximal portion of the continuous wire is disposed about the proximal portion of the inner elongate member and the distal portion of the continuous wire is helically is disposed about the distal portion of the inner elongate tubular member;

an outer tubular member disposed about at least a part of the proximal portion of the inner elongate tubular member and helically wound coil, wherein a distal end of the outer tubular member is disposed proximate the transition region; and a distal tip portion extending over and surrounding the distal portion of the inner elongate member, the distal tip portion having a proximal end abutting the distal end of the outer tubular member.

11. The elongate medical device of claim 10, wherein the proximal cross-sectional profile has a cross-sectional area greater than that of the distal cross-sectional profile.

12. The elongate medical device of claim 10, wherein the proximal portion of the helically wound continuous wire extends over a majority of the length of the inner elongate member.

* * * * *